(12) United States Patent
Kim et al.

(10) Patent No.: US 10,251,824 B2
(45) Date of Patent: Apr. 9, 2019

(54) METHOD FOR INDUCING PLURIPOTENT STEM CELLS AND PLURIPOTENT STEM CELLS PREPARED BY SAID METHOD

(71) Applicants: AMOREPACIFIC CORPORATION, Seoul (KR); SNU R&DB FOUNDATION, Seoul (KR)

(72) Inventors: Ah Reum Kim, Yongin-si (KR); Su Na Kim, Yongin-si (KR); Won Seok Park, Yongin-si (KR); Yoo Wook Kwon, Seoul (KR); Young Bae Park, Seoul (KR); Hyo Soo Kim, Seoul (KR); Jae Seung Paek, Ansan-si (KR)

(73) Assignees: AMOREPACIFIC CORPORATION, Seoul (KR); SNU R&DB FOUNDATION, Seoul (KR)

(*) Notice: Subject to any disclaimer, the term of this patent is extended or adjusted under 35 U.S.C. 154(b) by 0 days.

(21) Appl. No.: 15/377,464

(22) Filed: Dec. 13, 2016

(65) Prior Publication Data

US 2017/0128336 A1    May 11, 2017

Related U.S. Application Data

(62) Division of application No. 14/779,136, filed as application No. PCT/KR2014/009702 on Oct. 16, 2014, now abandoned.

(30) Foreign Application Priority Data

Oct. 17, 2013    (KR) .................... 10-2013-0123860

(51) Int. Cl.
| | |
|---|---|
| *A61K 8/365* | (2006.01) |
| *A61Q 19/00* | (2006.01) |
| *A23L 33/105* | (2016.01) |
| *A61K 35/28* | (2015.01) |
| *C12N 5/074* | (2010.01) |
| *A61K 31/191* | (2006.01) |
| *A61K 36/14* | (2006.01) |
| *A61Q 19/08* | (2006.01) |

(Continued)

(52) U.S. Cl.
CPC ............ *A61K 8/365* (2013.01); *A23L 2/52* (2013.01); *A23L 33/10* (2016.08); *A23L 33/105* (2016.08); *A61K 8/0204* (2013.01); *A61K 8/0216* (2013.01); *A61K 8/0225* (2013.01); *A61K 8/06* (2013.01); *A61K 8/11* (2013.01); *A61K 8/368* (2013.01); *A61K 8/97* (2013.01); *A61K 8/981* (2013.01); *A61K 9/0019* (2013.01); *A61K 9/0056* (2013.01); *A61K 9/0095* (2013.01); *A61K 9/14* (2013.01); *A61K 9/20* (2013.01); *A61K 9/48* (2013.01); *A61K 31/191* (2013.01); *A61K 35/28* (2013.01); *A61K 36/14* (2013.01); *A61Q 19/00* (2013.01); *A61Q 19/08* (2013.01); *C12N 5/0696* (2013.01); *A23V 2002/00* (2013.01); *A61K 2800/74* (2013.01); *A61K 2800/78* (2013.01); *A61K 2800/91* (2013.01); *A61K 2800/92* (2013.01); *C12N 2500/14* (2013.01); *C12N 2500/76* (2013.01); *C12N 2501/115* (2013.01); *C12N 2501/603* (2013.01); *C12N 2501/73* (2013.01); *C12N 2502/02* (2013.01); *C12N 2502/13* (2013.01); *C12N 2506/02* (2013.01); *C12N 2506/1307* (2013.01); *C12N 2533/54* (2013.01)

(58) Field of Classification Search
None
See application file for complete search history.

(56) References Cited

U.S. PATENT DOCUMENTS

| | | |
|---|---|---|
| 2003/0013192 A1 | 1/2003 | Laeng et al. |
| 2008/0095866 A1 | 4/2008 | Declercq et al. |
| 2011/0256626 A1 | 10/2011 | Park et al. |

FOREIGN PATENT DOCUMENTS

| | | | |
|---|---|---|---|
| JP | 2009215266 A | * | 9/2009 |
| KR | 1019980034293 A | | 8/1998 |

(Continued)

OTHER PUBLICATIONS

Note for Guidance on Quality of Water for Pharmaceutical Use (The European Agency for the Evaluation of Medicinal Products, May 2002, http://www.ema.europa.eu/docs/en_GB/document_library/Scientific_guideline/2009/09/WC500003394.pdf).*
Bianchi et al. (IT1392474B1, published Mar. 9, 2012; STN English abstract provided).*
Ana Belen Alvarez Palomo, et al., "Plant Hormones Increase Efficiency of Reprogramming Mouse Somatic Cells to Induced Pluripotent Stem Cells and Reduce Tumorigenicity", Stems Cells and Development, vol. 23, No. 6 (2014), pp. 586-593.

(Continued)

*Primary Examiner* — Dennis Heyer
*Assistant Examiner* — Daniel M Podgorski
(74) *Attorney, Agent, or Firm* — Cantor Colburn LLP

(57) ABSTRACT

The present disclosure relates to a method for inducing pluripotent stem cells by inducing reprogramming and/or dedifferentiation of differentiated adult cells using shikimic acid, a plant extract or plant stem cells containing shikimic acid and an extract of dedifferentiated stem cells (callus), pluripotent stem cells prepared by the method and a composition containing the pluripotent stem cells. In accordance with the present disclosure, ethical concerns implicated with the use of eggs to prepare pluripotent stem cells such as embryonic stem cell can be resolved. And, because the plant stem cell extract unharmful to human is used, pluripotent stem cells with proven safety can be prepared and they may be used to develop immunocompatible cell therapy agents suited for individuals. In addition, by pluripotent stem cells from individuals having diseases, the present disclosure will be very useful in studying the cause of diseases and devolving therapeutic strategy.

3 Claims, 17 Drawing Sheets

(51) Int. Cl.
A61K 8/368 (2006.01)
A61K 8/97 (2017.01)
A23L 33/10 (2016.01)
A23L 2/52 (2006.01)
A61K 8/02 (2006.01)
A61K 8/06 (2006.01)
A61K 8/11 (2006.01)
A61K 8/98 (2006.01)
A61K 9/00 (2006.01)
A61K 9/14 (2006.01)
A61K 9/20 (2006.01)
A61K 9/48 (2006.01)

(56) References Cited

FOREIGN PATENT DOCUMENTS

| | | |
|---|---|---|
| KR | 1020090104223 A | 10/2009 |
| KR | 1020110032989 A | 3/2011 |
| KR | 1011218830000 A | 3/2012 |
| KR | 1020120058829 A | 6/2012 |

OTHER PUBLICATIONS

Denis V. Bochkov et al., "Shikimic acid: review of its analytical, isolation, and purification techniques from plant and microbial sources", J Chem Biol, vol. 5, (2012), p. 5-17.
International Search Report for International Application No. PCT/KR2014/009702 dated Jan. 16, 2015.
Partial Supplementary Search Report (Partial SSR)—European Application No. 14853540.4 dated Jul. 4, 2016, citing enumerated references listed within.
Susumu Miyazaki et al., "Emerging Methods for Preparing iPS Cells", Jpn J Clin Oncol, (2012), vol. 42, No. 9, pp. 773-779.
Written Opinion for International Application No. PCT/KR2014/009702 dated Jan. 16, 2015.
Xu, et al., ES Cell Extract-Induced Expression of Pluripotent Factors in Somatic Cells, The Anatomical Record, vol. 292, (2009) pp. 1229-1234.
European Office Action—European Application No. 14853540.4 dated May 3, 2017, citing references listed within.
Haruko Obokata et al., "Stimulus-triggered fate conversion of somatic cells into pluripotency", Nature, vol. 505, Jan. 30, 2014, pp. 641-647.
Extended European Search Report for Application No. 17164428-1402 dated Oct. 25, 2017.
Rawat, et al., Expanding horizons of shikimic acid, Recent progresses in production and its endless frontiers in application and market trends, Applied Microbiology and Biotechnology, (2013), vol. 97, No. 10, pp. 4277-4287.
Saxena, et al., Pandemism of swine flu and its prospective drug therapy, European Journal of Clinical Microbiology & Infectious Diseases, (2012), vol. 31, No. 12, pp. 3265-3279.
King, et al., Protective Effects of 3, 4-Oxo-isopropylidene-Shikimic Acid on Experimental Colitis Induced by Trinitrobenzenesulfonic Acid in Rats, Digestive Diseases and Sciences, (2012), vol. 57, No. 8, pp. 2045-2054.
Japanese Office Action—Japanese Application No. 2016-548991 dated Aug. 28, 2018, citing reference listed within.
Method for Human iPS Cells Using Episomal Vector, Posted Apr. 4, 2011, pp. 1-5, Retrieved from the Internet Aug. 8, 2018, < https://www.cira.kyoto-u.ac.jp/research/img/protocol/Episomal_Protocol.pdf>.

* cited by examiner hES: Human embryonic stem cells
hiPS: Human induced pluripotent stem cells induced by plant stem cell extract

METHOD FOR INDUCING PLURIPOTENT STEM CELLS AND PLURIPOTENT STEM CELLS PREPARED BY SAID METHOD

CROSS REFERENCE TO RELATED APPLICATIONS

This application is a divisional of U.S. application Ser. No. 14/779,136, filed on Sep. 22, 2015, which is a National Stage application of PCT/KR2014/009702, filed Oct. 16, 2014, which claims the benefit of Korean Patent Application No. 10-2013-0123860, filed on Oct. 17, 2013, each of which is incorporated by reference in their entirety herein.

TECHNICAL FIELD

The present disclosure relates to a method for inducing pluripotent stem cells by reprogramming and/or dedifferentiating a differentiated adult cells, pluripotent stem cells prepared by the method and a composition containing the pluripotent stem cells.

The present disclosure also relates to a pharmaceutical composition or a cosmetic composition containing pluripotent stem cells.

The present disclosure also relates to a composition for activating stem cells, proliferating skin cells, regenerating skin or anti-aging.

BACKGROUND ART

Stem cells are undifferentiated cells that can differentiate into various types of cells constituting biological tissues and can be obtained from the tissues of embryos, fetuses and adults. Among the different cell types of the stem cell, pluripotent stem cells refer to the stem cells that can differentiate into any of the three germ layers, i.e., the endoderm, mesoderm and ectoderm.

The stem cells can be classified based on their anatomical sites, cellular functions, antigens presented on the cell surface, transcription factors, proteins produced by the cells, and specific cell types that can be derived from the stem cells.

As a rather clear criterion of classification, the stem cells can be classified based on their origin. Embryonic stem cells (ES cells) are isolated from embryos and adult stem cells are isolated from adult tissues.

Alternatively, the stem cells can be classified into pluripotent, multipotent and unipotent stem cells based on their capacity to differentiate into specialized cell types. In general, embryonic stem cells (ES cells) can be classified as pluripotent stem cells and adult stem cells can be classified as multipotent and unipotent stem cells.

The embryonic stem cells (ES cells) derived from the inner cell mass of a blastocyst, an early-stage embryo, are pluripotent stem cells that can differentiate into all the tissues constituting the adult body. That is to say, the embryonic stem cells are undifferentiated cells that can proliferate without limit and can differentiate into all cell types. Unlike the adult stem cells, they can be inherited to the next generation because they can form germ cells.

However, the pluripotent embryonic stem cells raise serious religious and ethical concerns implicated with the destruction of embryos during preparation thereof. In addition, since they are derived from limited embryos, immune rejection due to lack of immunocompatability between individuals cannot be avoided. To overcome these problems, there have been various attempts to artificially prepare pluripotent stem cells such as induced embryonic stem cells or embryonic stem cells using the cells derived from adults.

Typical examples include somatic cell nuclear transfer (SCNT), fusion with ES cells and reprogramming by defined factors. The somatic cell nuclear transfer is very inefficient and there is an ethical question in that it requires eggs in large quantities. The fusion with ES cells has a serious problem in terms of cell stability because the induced cells additionally have two pairs of genes. The reprogramming by defined factors, which has been reported most recently, involves the serious problem of carcinogenesis because it uses oncogene-containing viruses.

Therefore, a method for preparing induced pluripotent stem cells with proven stability and safety without raising ethical problems is needed for the development of a cell therapy agent.

To satisfy this need, a method for inducing induced pluripotent stem cells through dedifferentiation by introducing four genes into somatic cells was studied (Takahashi K, Yamanaka S (2006). Induction of pluripotent stem cells from mouse embryonic and adult fibroblast cultures by defined factors. *Cell* 126: 663-676). This method is free from ethical concerns because adult cells are used and the immune rejection problem is solved because autologous cells are used.

The inventors of the present disclosure have acquired dedifferentiated stem cells from an extract of animal-derived induced pluripotent stem cells (iPS) but there are some limitations.

First, a large quantity (20 mg or more) of iPSC extract is necessary for this method. For this reason, induction of dedifferentiation using an extract of human-derived dedifferentiated stem cells, which is costly and requires much labor, has not been successful. For example, to prepare human-derived dedifferentiated stem cells for obtaining 20 mg of extract, an expert has to work hard for at least 3 months, which is very costly.

Second, when somatic cells to be induced are treated with an extract of animal stem cells or dedifferentiated stem cells thereof, if the cells survive in the extract without being completely destroyed, it is not easy to distinguish the dedifferentiation-induced cells from the surviving dedifferentiated stem cells and analysis of genomic DNA is necessary, which is costly and time-consuming.

Third, since preparation of human-derived dedifferentiated stem cells using proteins has been hardly successful, an extract of human-derived dedifferentiated stem cells prepared using viruses has to be used. Because the resulting cells may contain oncogenic substances derived from the viruses, there may be difficulty in clinical application.

DISCLOSURE

Technical Problem

In an aspect, the present disclosure is directed to providing a method for preparing pluripotent stem cells with proven stability and safety without raising ethical problems in order to solve the problems in the related art. The present disclosure is also directed to providing a method for inducing human-derived dedifferentiated stem cells, which has been hardly successful.

The inventors of the present disclosure have developed a method for inducing pluripotent stem cells using cells derived from an adult, so that the pluripotent stem cells have the same genetic background as the adult. According to the present disclosure, the same result can be obtained from adult-derived cells having various genetic backgrounds. Accordingly, the method of the present disclosure is suitable for preparation of pluripotent stem cells.

Technical Solution

In an aspect, the present disclosure provides a method for inducing stem cells, including treating adult-derived cells with shikimic acid, a plant extract containing shikimic acid, a plant stem cell extract containing shikimic acid, or a composition containing them.

Specifically, in an aspect, the present disclosure provides a method for preparing induced pluripotent stem cells, including extracting an extract containing active ingredients from plant stem cells or any type of induced pluripotent plant stem cells induced by various methods; injecting the extract into adult-derived cells; and preparing pluripotent cells such as embryonic stem cells by culturing the cells into which the extract has been injected.

In another aspect, the present disclosure provides a method for preparing stem cells, which further includes injecting shikimic acid, a plant extract containing shikimic acid, a plant stem cell extract containing shikimic acid, or a composition containing them into adult-derived cells; and culturing the cells into which the shikimic acid, the extract or the composition has been injected.

The extract may be a callus extract.

In an exemplary embodiment of the present disclosure, the method may further include, before the injection of the extract, treating the adult-derived cells with a cell membrane permeabilizing agent. The cell membrane permeabilizing agent may include streptolysin O and digitonin, although not being limited thereto as long as it allows easy injection of the shikimic acid or the extract according to the present disclosure through the cell membrane.

In another exemplary embodiment of the present disclosure, the method may further include culturing the adult-derived cells into which the extract has been injected after transferring to a feeder cell layer. The feeder cells may include STO cells, although not being limited thereto.

In another aspect, the present disclosure provides a method for preparing induced pluripotent stem cells, including extracting an extract containing active ingredients from plant stem cells, a callus or any type of induced pluripotent plant stem cells induced by various methods; injecting the extract into adult-derived cells; culturing the cells into which the extract has been injected using normal cell culture media; and further culturing the cells using embryonic stem cell culture media after transferring to a feeder cell layer.

In another aspect, the present disclosure provides stem cells prepared by the above-described method.

In another aspect, the present disclosure provides a composition containing the stem cells. In another aspect, the present disclosure provides a method for inducing inducible pluripotent stem cells (iPSC) by inducing reprogramming and/or dedifferentiation of differentiated adult cells using shikimic acid or a plant extract or a plant stem cell extract containing the same, pluripotent stem cells prepared by the method, and a cell therapy agent containing the pluripotent stem cells.

The plant extract or plant stem cell extract containing shikimic acid used in the present disclosure may further contain an extract of one or more selected from a group consisting of *sequoia* (*Sequoiadendron giganteum*), *Iris pseudoacorus*, *Helianthus tuberosus*, *Picea pungens*, *Picea glauca*, *Eucalyptus sieberiana*, *Eucalyptus regnans*, *Thuja plicata*, *Phoenix dactylifera*, *Dahlia variabilis*, *Malus bac-cata*, *Pyrus communis*, *Triticum*, *Pinus densifloraa*, *Pinus thunbergii*, *Illicium anisatum*, *Magnolia grandiflora*, *Houttuynia cordata*, *Saxifraga stolonifera*, *Terminalia arjuna*, *Pistacia lentiscus*, *Ribes aureum*, *Symphytum officinalis*, *Actaea pachypoda*, *Alangium salvifollium*, *Gingko biloba*, *Veratrum viride*, *Dipsacus laciniatus*, *Agastache urticifolia*, *Inula helenium*, *Hypericum* spp., *Commelina bengalensis*, *Gymnema sylvestris*, *Terminalia chebula*, *Illicium floridanum*, *Illicium diffengri*, *Illicium henryi*, *Illicium verum*, *Illicium lancealatum*, *Illicium pachyphyllum*, *Illicium anisaturn*, *Illicium religiosum*, *Hemidesmus indicus*, *Cistus incanus*, *Sida acuta*, *Celastrus paniculata*, *Glycosmis muricata*, *Tanacetum parthenium*, *Triticum aestivum*, *Hypericum dolabriforme*, *Dipsacus pilosus*, *Triadenum walteri*, *Hypericum flondosum* and *Terminalia pallid* (Denis V. Bochkov et. al., Shikimic acid: review of its analytical, isolation, and purification techniques from plant and microbial sources, *J Chem. Biol.* (2012) 5; 5-17).

In another aspect, the present disclosure provides a composition for activating stem cells, regenerating skin or anti-aging, which contains the stem cells prepared by the above-described method, or a pharmaceutical or cosmetic composition containing the same.

Advantageous Effects

In accordance with the present disclosure, an extract of plant stem cells or any type of induced pluripotent plant stem cells induced by various methods, shikimic acid, a plant extract containing shikimic acid, or a composition containing the same may be used to prepare stem cells. The method of the present disclosure is applicable to the cells of all species having various genetic backgrounds, including human. In addition, the method of the present disclosure is free from ethical concerns because it uses a plant-derived stem cell extract and allows for preparation of induced pluripotent stem cells with proven safety.

BRIEF DESCRIPTION OF DRAWINGS

FIG. 4 B shows typical embryonic stem cells.

FIG. 6 B shows human pluripotent stem cells induced by using four factor viruses of Yamanaka as well as a result of alkaline phosphatase staining thereof.

BEST MODE

Figure 1:
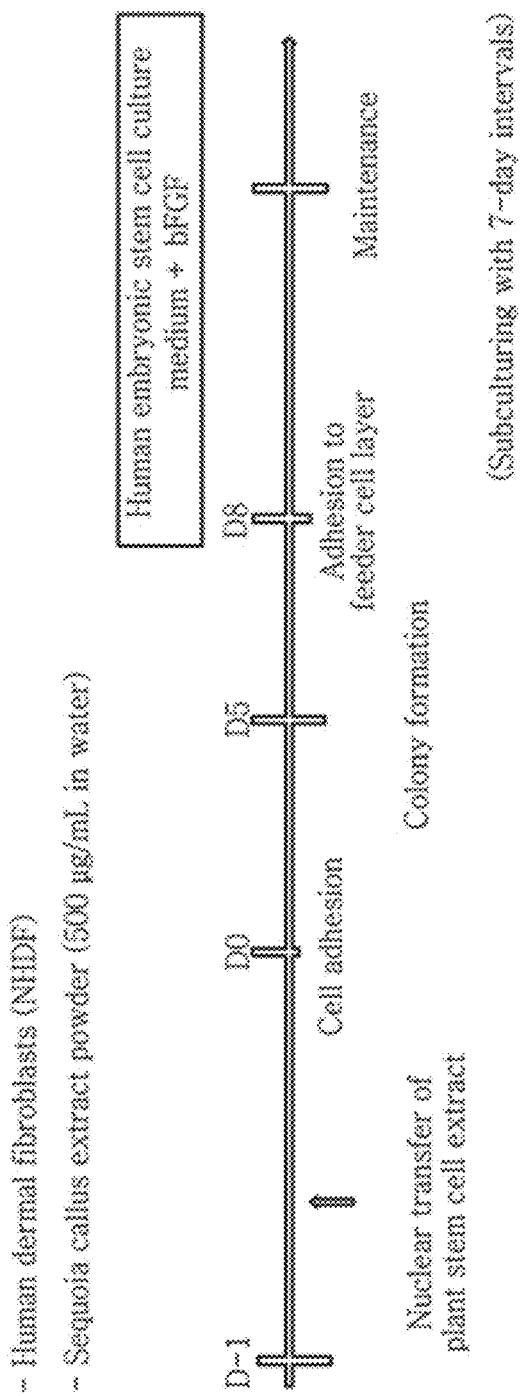
FIG. 1 schematically describes an experimental procedure of inducing pluripotent stem cells according to the present disclosure.

Korean Patent Application No. 10-2013-0123860, which was filed on Oct. 17, 2013 is incorporated herein in its entirety for all purposes. In addition, this application claims the priority of Korean Patent Application No. 10-2013-0123860 and all the benefits accruing therefrom, the contents of which in its entirety are herein incorporated by reference.

In an aspect, the present disclosure provides a method for preparing induced pluripotent stem cells, including:

a) a step of extracting an extract containing active ingredients from plant stem cells or induced pluripotent plant stem cells;

b) a step of injecting the extract into adult-derived cells; and c) a step of preparing pluripotent cells such as embryonic stem cells by culturing the cells into which the extract has been injected.

In another aspect, the present disclosure provides a method for preparing stem cells, including treating adult-derived cells with shikimic acid, a plant extract containing shikimic acid, a plant stem cell extract containing shikimic acid, or a composition containing them.

In another aspect, the present disclosure provides a method for preparing stem cells, including: injecting shikimic acid, a plant extract containing shikimic acid, a plant stem cell extract containing shikimic acid, or a composition containing them into adult-derived cells; and culturing the cells into which the shikimic acid, the extract or the composition has been injected.

In the present disclosure, the extract may be a callus extract.

In an aspect of the present disclosure, the plant extract or the plant stem cell extract may contain shikimic acid, caffeic acid or ferulic acid.

In the present disclosure, 'shikimic acid' may be represented by Chemical Formula 1 and is used in a broad concept, including its precursors, derivatives, etc. The shikimic acid may have a molecular weight of 174.15 g/mol.

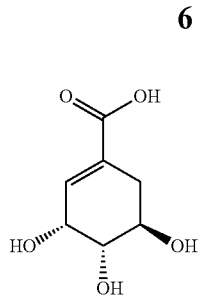

[Chemical Formula 1]

In the present disclosure, 'caffeic acid' may be represented by Chemical Formula 2 and is used in a broad concept, including its precursors, derivatives, etc. It may have a molecular weight of 180.16 g/mol. Caffeic acid is a phenolic compound contained in fruits including coffee bean and pear and medicinal plants such as basil, thyme, banana, tarragon, oregano, dandelion, etc.

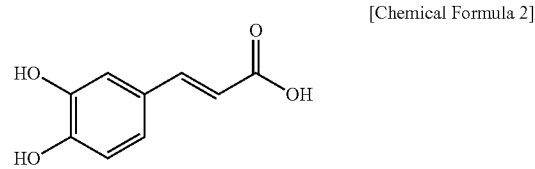 [SMILES: O=C(O)/C=C/c1ccc(O)c(O)c1]

[Chemical Formula 2]

In the present disclosure, 'ferulic acid' may be represented by Chemical Formula 3 and is used in a broad concept, including its precursors, derivatives, etc. It may have a molecular weight of 191.18 g/mol. Ferulic acid is a precursor to lignin constituting plant cell walls and is abundant in plant cell walls. It can be found in plant seeds of wheat, oats, coffee, apple, orange, peanut, etc.

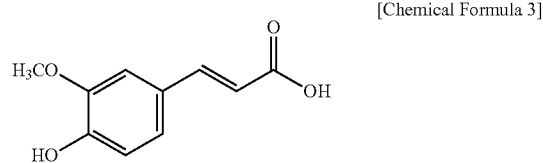 [SMILES: COc1cc(/C=C/C(=O)O)ccc1O]

[Chemical Formula 3]

In the present disclosure, the term 'stem cell' refers to a master cell that can proliferate without limit so as to form cells specialized for various tissues and organs. The stem cells are developable pluripotent or multipotent cells. A stem cell may divide into two daughter stem cells or into one daughter stem cell and one transit cell. Afterwards, they proliferate as mature and complete cells of the tissues.

In the present disclosure, the term 'embryonic stem cell' refers to a pluripotent cell which is isolated from the inner cell mass of a blastocyst, an early-stage embryo, after fertilization and then cultured.

In the present disclosure, the term 'dedifferentiated stem cell or induced pluripotent stem cell (iPS) extract' refers to a substance obtained by finely chopping dedifferentiated stem cells or induced pluripotent stem cells (iPS), which have been induced and cultured by various methods, in a test tube using physical/chemical methods and then separating through centrifugation, etc.

In the present disclosure, the term 'plant stem cell' refers to a plant stem cell derived from a cambium. In particular, it includes physically intact pure cambial meristematic cells (CMC), found in the cambium at a boundary between the xylem and the phloem. In the present disclosure, the term 'plant stem cell' is used in the broad concept, including any type of induced pluripotent plant stem cells induced by various methods.

In the present disclosure, the term 'callus' refers to a mass of unorganized parenchyma cells, a typical example of which is a tumor tissue formed from a meristematic tissue around a plant wound. The plant tissues are largely divided into the meristematic tissues which show cell division and the permanent tissues which do not. When the cells of a meristematic issue is cultured in a nutrient medium, a callus is formed initially. Then, an adventitious embryo is formed and it is differentiated into a plant organ. The callus is commonly called 'plant stem cells'. The callus used in the present disclosure is not limited in its kind.

In the present disclosure, the term 'pluripotent stem cell' refers to a stem cell having the pluripotency to differentiate into any of the three germ layers of an organism, i.e. endoderm, mesoderm and ectoderm. Traditionally, embryonic stem cells are the stem cells in this category.

In the present disclosure, the term 'induced pluripotent stem cell' refers to a pluripotent stem cell which is genetically identical to a donor cell used to prepare the induced pluripotent stem cell. That is to say, the induced pluripotent stem cell originates from the donor cell.

In the present disclosure, the terms 'induced pluripotent stem cell,' 'dedifferentiated stem cell' and inducible pluripotent stem cell can be used interchangeably.

In the present disclosure, the term 'adult-derived cell' refers, as opposed to an embryonic cell, to a cell which is derived from a surviving adult.

In the present disclosure, the term 'differentiation' refers to a process by which the morphology or function of a cell is specialized during it divides and proliferates. The morphology or function of the cell changes so as to perform specific functions of the cell, tissue, etc. of an organism. In general, it refers to a phenomenon by which a relatively simple system is divided into two or more qualitatively different sub-systems. That is to say, occurrence of differences from an essentially identical part of an organism or division to qualitatively different systems as a result thereof, such as formation of head or body parts from an egg during ontogenesis or differentiation of muscle cells, neural cells, etc., is called differentiation.

In an aspect of the present disclosure, the plant may be *sequoia*.

In an aspect of the present disclosure, the plant stem cells may be a callus.

In an aspect of the present disclosure, the plant stem cells may be *sequoia* stem cells.

In an aspect of the present disclosure, the plant stem cell extract may be a callus extract.

In an aspect of the present disclosure, the extract may be a *sequoia* callus extract.

In an aspect of the present disclosure, the *sequoia* may be giant *sequoia* (*Sequoiadendron giganteum*).

In an aspect of the present disclosure, the extract or the composition may contain shikimic acid.

In an aspect of the present disclosure, the composition may contain the shikimic acid at a concentration of 10 μM to 30 mM based on the total volume of the composition. In another aspect of the present disclosure, the composition may contain the shikimic acid, the plant extract or the plant stem cell extract at a concentration of 10 μM or higher, 20 μM or higher, 30 μM or higher, 50 μM or higher, 100 μM or higher, 1 mM or higher, 5 mM or higher, 10 mM or higher, 20 mM or higher or 30 mM or higher, and 1 M or lower or 100 M or lower, based on the total volume of the composition. When the content of the shikimic acid contained in the composition is 10 μM or lower, it may be difficult to achieve the effect of the present disclosure. And, when it is 30 mM or higher, skin irritation may be caused. Specifically, the shikimic acid may be contained at a concentration of 0.1 mM or higher, 0.5 mM or higher, 0.6 mM or higher, 0.7 mM or higher, 0.8 mM or higher or 0.9 mM or higher, and 5 mM or lower, 4 mM or lower, 3 mM or lower, 2 mM or lower, 1.5 mM or lower, 1.4 mM or lower, 1.3 mM or lower, 1.2 mM or lower or 1.1 mM or lower, based on the total volume of the composition. More specifically, the shikimic acid may be contained at a concentration of 0.8-1.2 mM, based on the total volume of the composition. Most specifically, the shikimic acid may be contained at a concentration of 1 mM, based on the total volume of the composition.

In an aspect of the present disclosure, the plant extract or the plant stem cell extract may contain the shikimic acid at a concentration of 0.0001-45% (w/v) based on the total volume of the extract. When the shikimic acid is contained in this range, superior Oct3/4 gene expressing effect, ALP expressing effect and fibroblast proliferation promoting effect may be achieved. In this aspect, in the present disclosure, the plant extract or the plant stem cell extract may contain the shikimic acid at a concentration of 0.001% (w/v) or higher, 0.01% (w/v) or higher, 0.1% (w/v) or higher, 1% (w/v) or higher, 5% (w/v) or higher, 10% (w/v) or higher, 15% (w/v) or higher, 20% (w/v) or higher, 25% (w/v) or higher or 30% (w/v) or higher, and 45% (w/v) or lower, 40% (w/v) or lower, 38% (w/v) or lower, 36% (w/v) or lower, 34% (w/v) or lower, 33% (w/v) or lower or 32% (w/v) or lower, based on the total volume of the extract. Specifically, in the present disclosure, the plant extract or the plant stem cell extract may contain the shikimic acid at a concentration of 32-34% (w/v), more specifically 32.75% (w/v), based on the total volume of the extract.

In an aspect of the present disclosure, the composition may contain the plant extract or the plant stem cell extract at such a concentration that the concentration of the shikimic acid contained in the extract is that described above based on the total volume of the composition. For example, the plant extract or the plant stem cell extract may be contained in the composition at a concentration of 0.001 μg/mL or higher, 0.01 μg/mL or higher, 0.1 μg/mL or higher, 1 μg/mL or higher, 10 μg/mL or higher, 50 μg/mL or higher, 100 μg/mL or higher, 0.3 mg/mL or higher, 0.4 mg/mL or higher, 0.5 mg/mL or higher, 0.6 mg/mL or higher, 0.7 mg/mL or higher, 1 mg/mL or higher, 1.5 mg/mL or higher, 2 mg/mL or higher, 5 mg/mL or higher, 10 mg/mL or higher, 20 mg/mL or higher or 50 mg/mL or higher, and 1 g/mL or lower or 10 g/mL or lower, based on the total volume of the composition.

In the present disclosure, the concentration of the shikimic acid contained in the plant extract or the plant stem cell extract may be measured using the Waters 1525μ Binary HPLC Pump and the Gemini 5u C18 110 A column (5 μm, 4.60 mm×250 nm, Phenomenex), using solvent A (water, containing 0.1% TFA) and solvent B (acetonitrile, containing 0.1% TFA) as mobile phases.

In the present disclosure, '*sequoia*' includes redwood (*Sequoia sempervirens*), giant *sequoia* (*Sequoiadendron giganteum*) or metasequoia (*Metasequoia glyptostroboides*).

Redwood (*Sequoia sempervirens*) is a tree of the family Cupressaceae, order Pinales. It grows only in the northwestern coastal California and the southwestern coastal Oregon within the United States and in New Zealand. It lives about 2500-3000 years and is the tallest tree in the world, reaching up to 112 m. It is 2.5-4.5 m in diameter and 50-100 m in height and the bark can be very thick, up to 20-30 cm. The leaves, which are similar to those of yew trees, are 1-3 cm long, with pointed tips and distinct main veins. They are dark green above and whitish below.

Giant *sequoia* (*Sequoiadendron giganteum*) is the sole living species in the genus *Sequoiadendron*. It grows in the western slopes of the Sierra Nevada Mountains of California, at 1500-2500 m above the sea level. It reaches 3.5-6 m in diameter and 60-90 m in height and the diameter near the root is around 10 m. The leaves are similar to those of cedar. They are about 1 cm long and arranged spirally. But, the leaves on mature branches are scale-shaped.

*Metasequoia* (*Metasequoia glyptostroboides*) is the sole living species in the genus *Metasequoia*, family Cupressaceae. It grows up to 35 m in height. The grayish brown bark is vertically fissured. The branches spread sideways and the leaves are opposite, 10-23 mm in length and 1.5-2 mm in width. The pointed leaves turn reddish brown in fall. The flowers bloom moneciously in February to March. The male flowers hang in racemes from the tip of the branches at the axils and have 20 stamens. The female flowers hang on the tip of the branches and bloom in March. The cones are globose, 18-25 mm in length. They ripen brown and produce winged oval seeds. The deciduous conifer tree is native to Sichuan and Hubei provinces of China and is distributed in Korea, China, etc. It is mainly planted as park trees.

A callus refers to a mass of undifferentiated, unorganized parenchyma cells, a typical example of which is a tumor tissue formed from a meristematic tissue around a plant wound. The plant tissues are largely divided into the meristematic tissues which show cell division and the permanent tissues which do not. When the cells of a meristematic issue is cultured in a nutrient medium, a callus is formed initially. Then, an adventitious embryo is formed and it is differentiated into a plant organ. The callus is commonly called "plant stem cells".

In the present disclosure, the 'extract' includes any substance extracted from a natural product, regardless of extraction method, extraction solvent, extracted components or type of extract. It is used in a broad concept, including the substance obtained by processing or treating otherwise the extract.

In the present disclosure, the *sequoia* may be used in the form of an extract, a pulverization product of the plant or a dried pulverization product of the plant, although not being limited thereto. Besides, the *sequoia* used in the present disclosure is not limited as to how it is obtained. It may be either cultivated or purchased commercially and may be the aerial part, underground part or both of *sequoia*. The aerial part may include the fruit, leaf and stem of *sequoia* and the underground part may include the root, although not being limited thereto.

In the present disclosure, the 'plant extract' includes any substance extracted from the plant such as *sequoia*, regardless of extraction method, extraction solvent, extracted components or type of extract. It is used in a broad concept, including the substance extracted by treating with heat, an acid, a base, an enzyme, etc. as well as the substance obtained by processing or treating otherwise the extract of *sequoia*.

In the present disclosure, the 'plant stem cell extract' includes any substance obtained by culturing the plant stem cells of *sequoia*, etc. and extracting its active ingredients, regardless of extraction method, extraction solvent, extracted components, type of extract, etc. It is used in a broad concept, including any substance extracted from the active ingredients of the plant stem cells of *sequoia*, etc. by treating with heat, an acid, a base, an enzyme, etc. as well as the substance obtained by processing or treating otherwise the extract of *sequoia*.

The method of the present disclosure includes a step of culturing plant stem cells or induced pluripotent plant stem cells induced by various methods and preparing an extract therefrom, which may be conducted by a method known in the art. For example, after culturing plant stem cells or induced pluripotent plant stem cells induced by various methods, they may be treated with a protease and then the supernatant may be collected. Alternatively, plant stem cells may be incubated at 65° C. for 2 hours and then filtered to extract the proteins derived from each cell or shikimic acid. In an exemplary embodiment of the present disclosure, a callus powder may be used.

In the present disclosure, the *sequoia* callus extract may be obtained through i) a step of inducing a callus from *sequoia*; ii) step of establishing a stem cell line by culturing the callus in a solid medium; iii) a step of producing active ingredients in large scale by suspension culturing the cell line; and iv) a step of extracting the produced active ingredients.

In the present disclosure, the extraction of the active ingredients from the *sequoia* callus may be performed by culturing of a cell line derived from a tissue explant of the plant as described in Korean Patent Publication No. 2007-0113193. Specifically, a stabilized plant cell line derived from *sequoia* may be extracted using a mixture of a $C_5$ or lower alcohol, although not being limited thereto.

Alternatively, the *sequoia* callus extract or the *sequoia* callus powder used in in the present disclosure may be purchased commercially.

In the present disclosure, the *sequoia* callus extract may be prepared by dissolving a *sequoia* callus powder in a solvent. The solvent may include one or more selected from a group consisting of water, an organic solvent and a mixture of water and an organic solvent. The water may include distilled water or purified water and the organic solvent may include an alcohol such as a $C_1$-$C_5$ lower alcohol, one or more selected from a group consisting of acetone, ether, ethyl acetate, diethyl ether, methyl ethyl ketone and chloroform, hexane, methylene chloride, ethyl acetate, n-butanol, a mixture solvent of butylene glycol (BG) and ethanol (EtOH), dimethyl sulfoxide (DMSO), etc., although not being limited thereto.

Those skilled in the art will easily understand that a high-concentration protein extract can be prepared using the existing protein extraction method. The concentration of the shikimic acid or the protein extract derived from the plant may be specifically 10 μg/mL to 1 mg/mL, more specifically about 500 μg/mL, based on the total volume of the composition containing the extract. When the concentration of the protein extract is outside the above range, the efficiency of inducing the induced pluripotent stem cells may decrease or the cells treated with the extract may die.

The method of the present disclosure includes a step of injecting a protein extract isolated from plant stem cells or induced pluripotent plant stem cells induced by various methods into adult-derived cells.

The adult-derived cells may include human dermal fibroblasts or neonatal human dermal fibroblasts.

For the injection, the cells may be permeabilized by treating with a cell membrane permeabilizing agent (e.g., streptolysin O or digitonin), so that the extract can be introduced into the cells. Following the permeabilization, the shikimic acid, the plant extract, the plant stem cell extract, the induced pluripotent plant stem extract or the composition is injected into the adult-derived cells through incubation.

In an aspect of the present disclosure, a method for preparing pluripotent stem cells may include:

1. a step of preparing shikimic acid, a plant extract containing shikimic acid, a plant stem cell extract or a composition containing the same according to the present disclosure;
2. a step of injecting the shikimic acid, the extract or the composition into adult-derived cells;
3. a step of culturing the adult-derived cells using a normal culture medium;
4. a step of further culturing the cells after transferring to a feeder cell layer; and
5. a step of recovering the cultured pluripotent stem cells.

Specifically, the step of injecting the shikimic acid, the extract or the composition into the adult-derived cells may include:

1. a step of separating adult-derived cells into individual cells and transferring to a tube after resuspending them;
2. a step of centrifuging the cells and resuspending the resulting cell pellets in a water bath;
3. a step of adding a cell membrane permeabilizing agent;
4. a step of performing reaction while mixing the sample in the water bath up and down;
5. a step of centrifuging the sample;
6. a step of resuspending the cell pellets using the shikimic acid, the extract or the composition;
7. a step of performing reaction while mixing the sample in the water bath up and down using an ATP regeneration system;
8. a step of adding an ES culture medium and performing incubation in an incubator; and
9. a step of cleansing and resuspending the cell pellets in an embryonic stem cell culture medium and then seeding onto a dish.

The method of the present disclosure includes a step of preparing pluripotent cells such as embryonic stem cells by culturing the cells into which the shikimic acid, the extract or the composition has been injected.

The method of the present disclosure may further include, after culturing the adult-derived cells into which the shikimic acid, the extract or the composition has been injected using a normal cell culture medium, a step of further culturing them after transferring to a feeder cell layer More specifically, after injecting the shikimic acid, the extract or the composition, the adult-derived cells may be cultured using a normal cell culture medium (DMEM, 5-15% FBS, 10-100 U/mL penicillin, 20-80 mg/mL streptomycin) until a colony is formed. After the colony has been formed, the cells may be transferred to a feeder cell layer and then subcultured in an embryonic stem cell culture medium with 5-8 day intervals while replacing the medium every day. The feeder cells used in the present disclosure may include STO cells, although not being limited thereto.

The pluripotent stem cells induced by the extract may be cultured in DMEM (Dulbecco's modified Eagle's medium)/F12 supplemented with 15-25% KSR (knockout serum replacement), 1-4 mM L-glutamine, 0.05-0.2 mM nonessential amino acids, 0.05-0.2 mM β-mercaptoethanol, 30-70 U/mL penicillin, 30-70 mg/mL streptomycin and 1-30 μg/mL bFGF. Those skilled in the art can easily recognize that the concentration of the compounds added to the DMEM can vary within the range at which the effect of the present disclosure can be achieved.

The present disclosure also provides a method for inducing induced pluripotent stem cells, including:

a) a step of preparing an extract by isolating proteins from plant stem cells or induced pluripotent plant stem cells induced by various methods;
b) a step of treating adult-derived cells with a cell membrane permeabilizing agent and then injecting the extract into the adult-derived cells; and
c) a step of culturing the extract-injected cells in a normal cell culture media and then culturing in an embryonic stem cell culture medium after transferring to a feeder cell layer.

The method of the present disclosure is characterized in that pluripotent stem cells which are hardly distinguishable from embryonic stem cells can be prepared from adult-derived cells using shikimic acid, a plant extract, plant stem cells, an extract of induced pluripotent plant stem cells induced by various methods or a composition containing the same.

The inventors of the present disclosure have confirmed that pluripotent stem cells are induced by the method of the present disclosure.

Figure 4A:
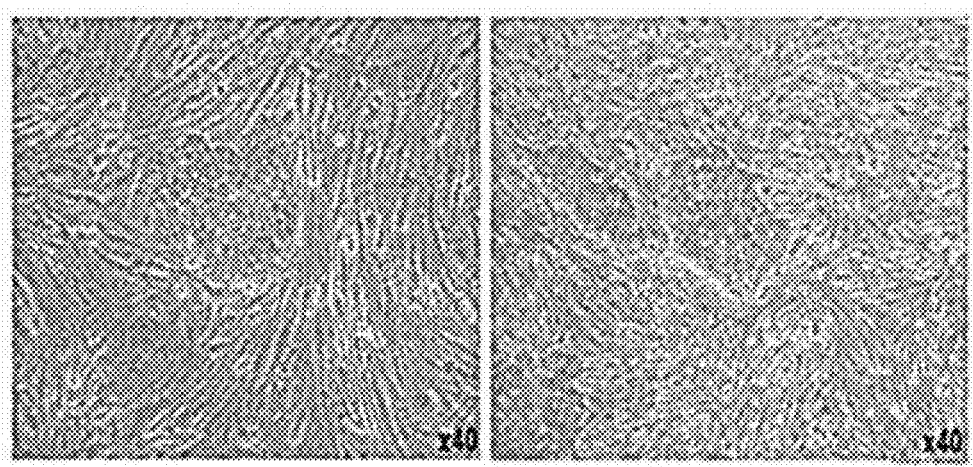
FIG. 4 A shows induced pluripotent stem cells observed on day 32 after treatment with a plant stem cell extract and after subculturing for 4 times after transfer to a feeder cell layer.
Figure 4B:
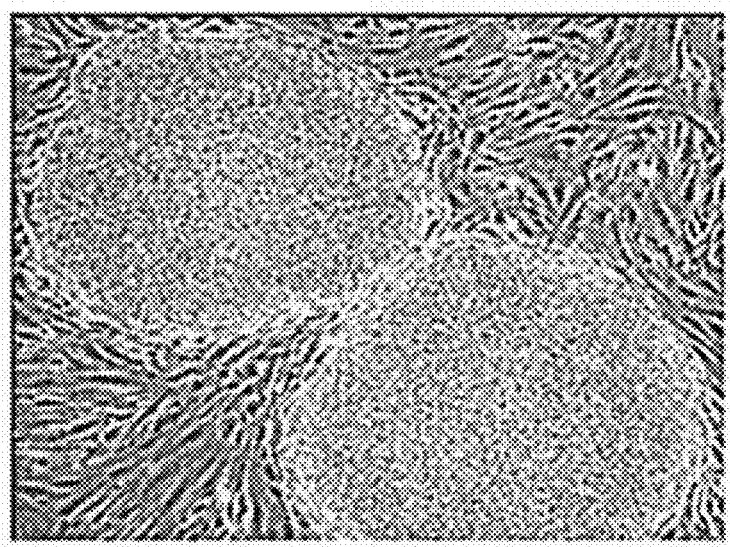

Specifically, the pluripotent stem cells induced by the method of the present disclosure are almost identical to embryonic stem cells in shape (see FIG. 4). In addition, investigation of the expression of the genes specific for embryonic stem cells (Nanog, Oct4) revealed that the genes are expressed in the pluripotent stem cells induced by the method of the present disclosure as in the embryonic stem cells (see FIG. 7 and FIG. 10).

In another aspect, the present disclosure provides induced pluripotent stem cells induced by the method according to an aspect of the present disclosure.

Figure 6A:
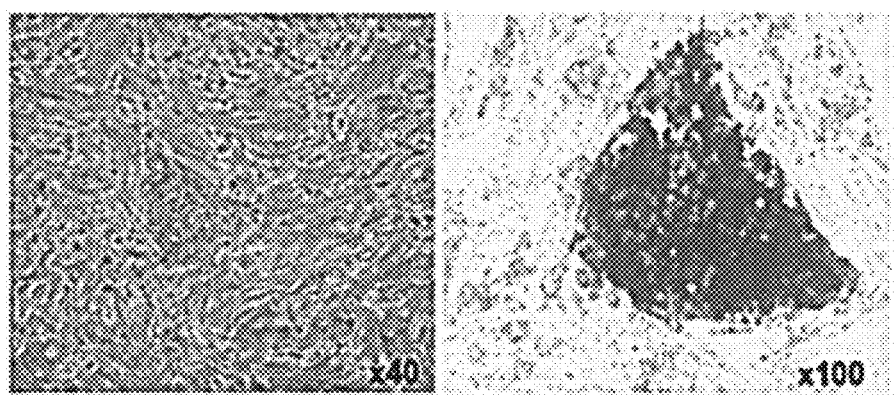
FIG. 6 A shows induced pluripotent stem cells observed on day 50 after treatment with a plant stem cell extract and after subculturing for 7 times after transfer to a feeder cell layer as well as a result of alkaline phosphatase staining thereof.
Figure 6B:
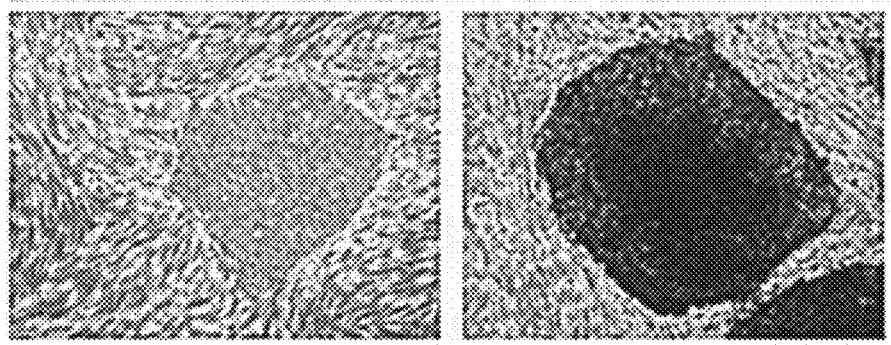

The inventors of the present disclosure have confirmed self-renewal, which is characteristic of stem cells, by performing subculturing 8-12 times using the method of the present disclosure (see FIG. 6).

In another aspect, the present disclosure provides a composition containing the pluripotent stem cells prepared by the method according to an aspect of the present disclosure.

In an aspect, the present disclosure provides a composition containing one or more of shikimic acid, a plant extract containing shikimic acid and a plant stem cell extract containing shikimic acid as an active ingredient.

In an aspect of the present disclosure, the composition may be a pharmaceutical composition, a food composition or a cosmetic composition.

In an aspect of the present disclosure, the composition may be a composition for activating stem cells, regenerating skin or anti-aging.

In an aspect, the present disclosure may relate to a method for activating stem cells, including a step of administering shikimic acid, a plant extract containing shikimic acid and a plant stem cell extract containing shikimic acid or a composition containing one or more of them to an individual in need of activation of stem cells. The administration may be performed according to the administration method or administration dose described in the present disclosure.

In an aspect, the present disclosure may relate to a method for regenerating skin, including a step of administering shikimic acid, a plant extract containing shikimic acid and a plant stem cell extract containing shikimic acid or a composition containing one or more of them to an individual in need of skin regeneration.

In an aspect, the present disclosure may relate to a method for anti-aging, including a step of administering shikimic acid, a plant extract containing shikimic acid and a plant stem cell extract containing shikimic acid or a composition containing one or more of them to an individual in need of anti-aging.

In an aspect, the present disclosure may relate to a use of shikimic acid, a plant extract containing shikimic acid and a plant stem cell extract containing shikimic acid or a composition containing one or more of them for activation of stem cells, skin regeneration or anti-aging.

In an aspect, the present disclosure may relate to shikimic acid, a plant extract containing shikimic acid and a plant stem cell extract containing shikimic acid or a composition containing one or more of them for use in activation of stem cells, skin regeneration or anti-aging.

In an aspect of the present disclosure, the composition may be a cell therapy agent.

Specifically, the cell therapy agent may be used for generation of hepatocytes, adipocytes, bone cells, cartilage cells, muscle cells, neurons, cardiac muscle cells, vascular endothelial cells, etc.

In an aspect, the present disclosure may relate to a method for cell therapy, including a step of administering shikimic acid, a plant extract containing shikimic acid and a plant stem cell extract containing shikimic acid or a composition containing one or more of them to an individual in need of cell therapy.

In an aspect, the present disclosure may relate to a use of shikimic acid, a plant extract containing shikimic acid and a plant stem cell extract containing shikimic acid or a composition containing one or more of them for cell therapy.

In an aspect, the present disclosure may relate to shikimic acid, a plant extract containing shikimic acid and a plant stem cell extract containing shikimic acid or a composition containing one or more of them for use in cell therapy.

As used in the present disclosure, the term 'cell therapy agent' refers to cells or tissues isolated from human and prepared as a medication through culturing and special operation for use in treatment, diagnosis and prevention (USFDA definition). It is used for the purpose of treatment, diagnosis and prevention by proliferating and screening living autologous, homologous or heterologous cells ex vivo or otherwise changing the biological properties of the cells to restore the function of cells or tissues. The cell therapy agents are largely classified into somatic cell therapy agents and stem cell therapy agents based on the degree of differentiation of the cells. The present disclosure relates particularly to the stem cell therapy agent.

In an aspect, the present disclosure provides a food composition, which contains the shikimic acid or the plant extract, the plant stem cell extract or the pluripotent stem cells containing shikimic acid according to an aspect of the present disclosure. In an aspect of the present disclosure, the composition may contain other ingredients within a range not negatively affecting the main effect desired by the present disclosure. For example, additives such as a fragrance, a pigment, a sterilizer, an antioxidant, a preservative, a humectant, a thickener, a mineral, an emulsifier, a synthetic polymer, etc. may be further included for improvement of physical properties. In addition, other adjuvant ingredients such as a water-soluble vitamin, an oil-soluble vitamin, a polypeptide, a polysaccharide, a seaweed extract, etc. may be further included. These ingredients may be adequately selected by those skilled in the art depending on the formulation type or purpose of use and the addition amount may be determined within a range not negatively affecting the purpose and effect of the present disclosure. For example, those ingredients may be added in an amount of 0.01-5 wt %, more specifically 0.01-3 wt %, based on the total weight of the composition. In an aspect of the present disclosure, the food composition may include a health food composition, a functional food composition, a nutritional supplement composition, a processed food composition, a food additive composition, etc., although not being limited thereto.

In an aspect, the present disclosure provides a cosmetic composition, which contains the shikimic acid or the plant extract, the plant stem cell extract or the pluripotent stem cells containing shikimic acid according to an aspect of the present disclosure. The cosmetic composition contains a cosmetically or dermatologically acceptable medium or matrix. The cosmetic composition may be in any form which is topically applicable, e.g., a solution, a gel, a solid, an anhydrous paste, an oil-in-water emulsion, a water-in-oil emulsion, a multiemulsion, a suspension, a microemulsion, a microcapsule, an ionic (liposome) or nonionic vesicular dispersion, a foam, an aerosol further containing a compressed propellant or a patch. These compositions may be prepared according to the methods commonly employed in the art.

The cosmetic composition may further contain, in addition to the above-described substances, other ingredients that may provide a synergic effect to the main effect within a range not negatively affecting the main effect. The other ingredients may be selected by those skilled in the art without difficulty depending on the formulation type or purpose of use. For example, the cosmetic composition of the present disclosure may contain, in addition to the active ingredient, other ingredients commonly mixed in a cosmetic composition. Examples include a fat, an oil, a humectant, an emollient, a surfactant, an organic or inorganic pigment, an organic powder, a UV absorbent, a preservative, a sterilizer, an antioxidant, a stabilizer, a thickener, glycerin, a pH control agent, an alcohol, a pigment, a fragrance, a blood circulation accelerator, a coolant, an antiperspirant, purified water, etc. However, the other ingredients that may be contained in the cosmetic composition are not limited thereto and the amount thereof may be determined within a range not negatively affecting the purpose and effect of the present disclosure.

The formulation type of the cosmetic composition is not particularly limited and may be selected adequately depending on purposes. For example, it may be prepared into one or more formulation selected from a group consisting of a softening lotion, a nourishing lotion, an essence, a nourishing cream, a massage cream, a pack, a gel, a makeup base, a foundation, a powder, a lipstick, a patch, a spray, an eye cream, an eye essence, a cleansing cream, a cleansing foam, a cleansing water, a cleanser, a hair shampoo, a hair conditioner, a hair treatment product, a hair essence, a hair lotion, a scalp and hair tonic, a scalp essence, a hair gel, a hair spray, a hair pack, a body lotion, a body cream, a body oil and a body essence, although not being limited thereto.

In an aspect, the present disclosure provides a pharmaceutical composition, which contains the shikimic acid or the plant extract, the plant stem cell extract or the pluripotent stem cells containing shikimic acid according to an aspect of the present disclosure. The pharmaceutical composition may further contain, in addition to the active ingredient, pharmaceutical adjuvants or other therapeutically useful substances such as a preservative, a stabilizer, a wetting agent, an emulsifier, a salt and/or buffer for control of osmotic pressure, a diluent (e.g., lactose, dextrose, sucrose, mannitol, sorbitol, cellulose or glycine), a lubricant (e.g., silica, talc, stearic acid and a magnesium or calcium salt thereof or polyethylene glycol), a binder (e.g., magnesium aluminum silicate, starch paste, gelatin, tragacanth, methyl cellulose, sodium carboxymethyl cellulose or polyvinylpyrrolidone), etc. In some occasions, it may further contain other pharmaceutical additives such as a disintegrant, e.g., starch, agar, alginic acid or a sodium salt thereof, an absorbent, a colorant, a flavor, a sweetener, etc.

The pharmaceutical composition may be prepared into formulations for oral or parenteral administration according to commonly employed methods.

Formulations for oral administration may include, for example, a tablet, a fill, a hard/soft capsule, a liquid, a suspension, an emulsion, a syrup, a powder, a dust, a fine granule, a granule, a pellet, etc. These formulations may contain, in addition to the active ingredient, a surfactant, a diluent (e.g., lactose, dextrose, sucrose, mannitol, sorbitol, cellulose and glycine), a lubricant (e.g., silica, talc, stearic acid and a magnesium or calcium salt thereof and polyethylene glycol). A tablet may contain a binder such as magnesium aluminum silicate, starch paste, gelatin, tragacanth, methyl cellulose, sodium carboxymethyl cellulose and polyvinylpyrrolidone and may further contain, in some cases, pharmaceutical additives, e.g., a disintegrant such as starch, agar, alginic acid or a salt thereof, an absorbent, a colorant, a flavor, a sweetener, etc. The tablet may be prepared by commonly employed mixing, granulation or coating methods.

Formulations for parenteral administration may include, for example, an injection, a drop, an ointment, a lotion, a gel, a cream, a spray, a suspension, an emulsion, a suppository, a patch, etc., although not being limited thereto.

The pharmaceutical composition according to an aspect of the present disclosure may be administered parenterally, e.g., rectally, topically, transdermally, subcutaneously, etc. The composition is prepared to be suitable for each formulation. In particular, a composition for intravenous injection is prepared with very high purity by excluding any unsuitable additive.

An administration dosage of the active ingredient will vary depending on the age, gender and body weight of a subject to be treated, the particular disease or pathological condition to be treated, administration route or the discretion of a diagnoser. The determination of the administration dosage considering these factors is within the level of those skilled in the art. Specifically, a general administration dose is from 30 µg/mL to 1 mg/mL, although not being limited thereto.

Specifically, in an aspect of the present disclosure, a pharmaceutical composition containing the pluripotent stem cells prepared by the method according to the present disclosure may be used as an injection. The pluripotent stem cells prepared by the method according to the present disclosure may be injected into the skin similarly to Botox, which is used to remove wrinkles, to activate skin stem cells and promote proliferation of skin cells, thereby resulting in skin generation, anti-aging, improvement of skin elasticity and improvement of wrinkles.

In another aspect, the present disclosure provides a reagent or medium composition for use in experiments, which contains the shikimic acid or the plant extract, the plant stem cell extract or the pluripotent stem cells containing shikimic acid according to an aspect of the present disclosure.

Hereinafter, the present disclosure will be described in detail through examples. However, the following examples are for illustrative purposes only and it will be apparent to those of ordinary skill in the art that the scope of the present disclosure is not limited by the examples.

[Example 1] Injection of Plant Cell Extract into Adult-Derived Cells

A callus powder was used as a plant-derived stem cell extract. The callus powder that can be used in the present disclosure is not particularly limited and a commercially available one may also be used.

A *sequoia* callus extract is obtained by inducing a callus from the leaf of *sequoia*, establishing a stem cell line by culturing the callus in a solid medium and producing active ingredients in large quantities through suspension culturing and then extracting the same. The extraction of the active ingredients from the *sequoia* callus can be performed by culturing of the cell line derived from the tissue explant of the plant as described in Korean Patent Publication No. 2007-0113193. Specifically, a stabilized plant cell line derived from *sequoia* may be extracted by dissolving in a mixture of a $C_5$ or lower alcohol, although not being limited thereto.

In this example, a *sequoia* callus powder commercially purchased from BIO-FD&C was used. Specifically, human dermal fibroblasts were separated into individual cells using trypsin-EDTA and then washed with cold PBS (phosphate buffered saline). The resulting cell pellets were resuspended in cold $Ca^{2+}$- and $Mg^{2+}$-free HBSS (Hank's balanced salt solution) with 100,000 cells/100 µL and then transferred to a 1.5-mL tube. After centrifuging at 120 g for 5 minutes at 4° C. using a horizontal swing-out rotor, the supernatant was discarded and the remaining cell pellets resuspended again in 97.7 µL of cold HBSS and incubated in a water bath at 37° C. for 2 minutes. Then, 2.3 µL of streptolysin O (SLO, 100 g/mL stock solution diluted 1:10 in cold HBSS) was added (final SLO concentration: 230 ng/mL). Alternatively, digitonin (20 µg/mL) and 200 µL of a transport solution (110 mM potassium acetate, 5 mM sodium acetate, 2 mM magnesium acetate, 1 mM EGTA, 2 mM DTT, protease inhibitor cocktail, 20 mM HEPES, pH 7.3) may be added instead of the SLO. The sample was incubated in a water bath at 37° C. for 50 minutes while mixing up and down with 10-minute intervals. After the incubation, the sample was placed on ice and centrifugation was carried out at 120 g for 5 minutes at 4° C. using a horizontal swing-out rotor after adding 200 µL of cold HBSS. After this permeabilization process, the resulting cell pellets were resuspended in 200 µL of a plant stem cell extract with 1000 cells/1 µL. A callus powder was used as the plant stem cell extract (500 µg/mL). Then, after adding 1 mM nucleotide triphosphate and ATP regeneration system (10 mM creatine phosphate and 25 g/mL creatine kinase) to the suspended cell pellets, incubation was conducted in a water bath at 37° C. for 1 hour while mixing up and down with 10-minute intervals. After the incubation, 1 mL of an ES medium containing 2 mM $CaCl_2$ was added and incubation was conducted in a 37° C. incubator for 2 hours for reconstitution of the plasma membrane. After washing with PBS, the cell pellets were resuspended in an embryonic stem cell culture medium and then seeded onto a dish coated with 0.1% gelatin.

[Example 2] Preparation of Pluripotent Cells Such as Embryonic Stem Cells by Culturing Extract-Injected Cells The extract-injected cells were incubated in a normal cell culture medium wherein DMEM (Dulbecco's modified Eagle's medium) was supplemented with 10% FBS, 50 U/mL penicillin and 50 mg/mL streptomycin in an incubator maintained at 37° C. and 5% $CO_2$. The adult-derived cells (human-derived dermal fibroblasts) into which the plant stem cell extract (callus powder) was injected were cultured on a dish coated with 0.1% gelatin. The medium was replaced after the first two days. After culturing for 10 days while replacing the medium every day, the cells were transferred to a feeder cell (STO cell) layer treated with mitomycin C (MMC) at a ratio of 1:2. Then, the cells were transferred to a new feeder cell layer with 7-day intervals while replacing DMEM (Dulbecco's modified Eagle's medium)/F12 supplemented with 20% KSR (knockout serum replacement), 2 mM L-glutamine, 0.1 mM nonessential amino acids, 0.1 mM β-mercaptoethanol, 50 U/mL penicillin, 50 mg/mL streptomycin and 10 μg/mL bFGF every day. It took about 21 days on average to culture induced stem cells necessary for analysis.

Figure 2:
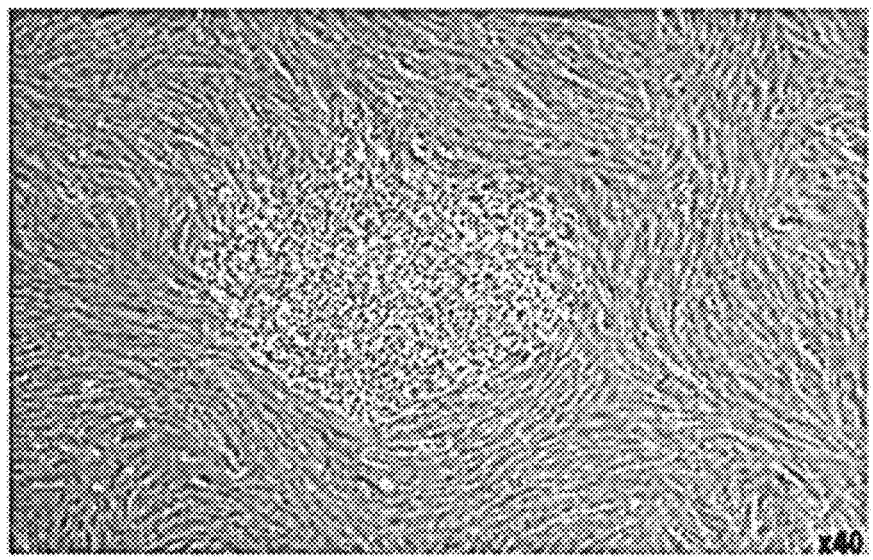
FIG. 2 shows induced pluripotent stem cells observed on day 5 after treatment with a plant stem cell extract.
Figure 3:
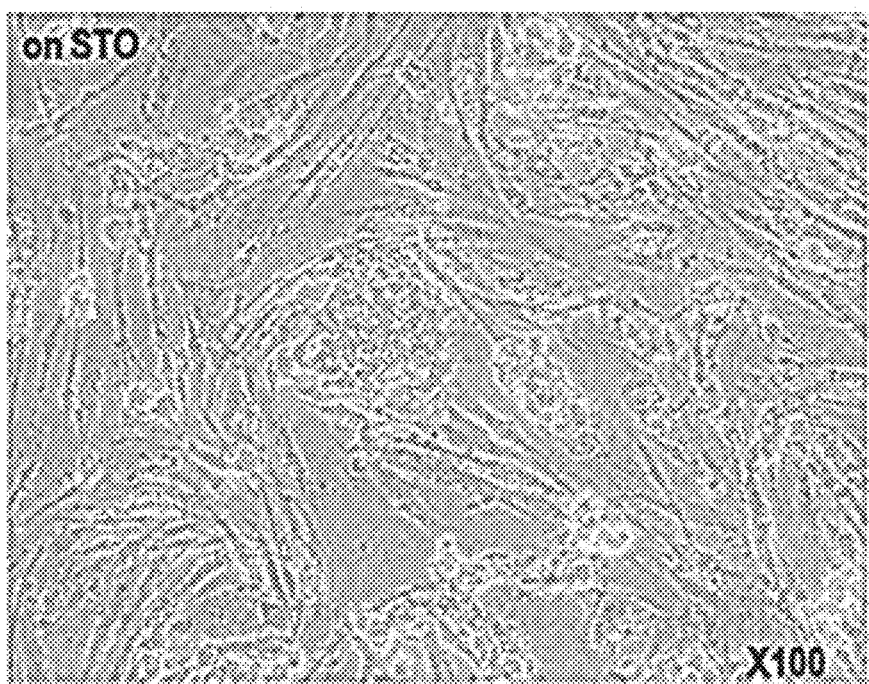
FIG. 3 shows induced pluripotent stem cells observed on day 8 after treatment with a plant stem cell extract and day 2 after transfer to a feeder cell layer.
Figure 5:
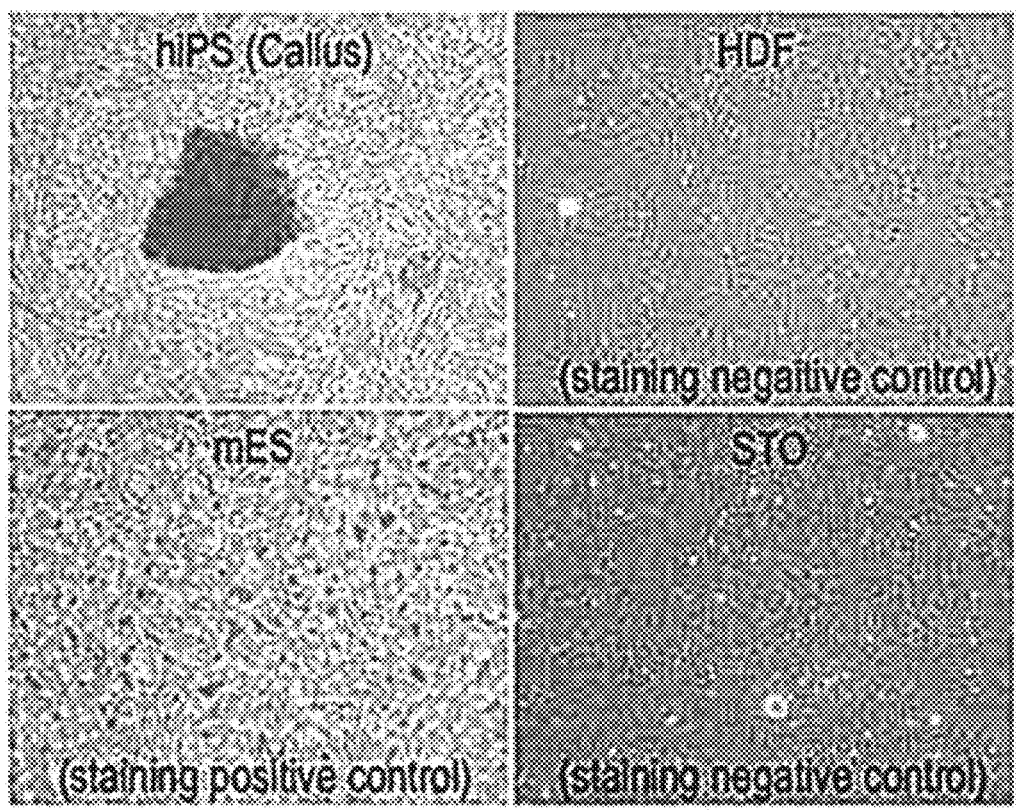
FIG. 5 shows a result of alkaline phosphatase staining of induced pluripotent stem cells observed on day 32 after treatment with a plant stem cell extract and after subculturing for 4 times after transfer to a feeder cell layer.

FIG. 1 schematically describes an experimental procedure of inducing pluripotent stem cells according to the method of the present disclosure. FIGS. 2-4 show induced pluripotent stem cells observed on days 5, 10 and 32 after culturing, respectively. And, FIGS. 5 and 6 show a result of alkaline phosphatase staining on days 32 and 50 after culturing, respectively. The alkaline phosphatase staining was carried out using a commonly used staining kit.

As seen from FIG. 6, the pluripotent stem cells induced according to the method of the present disclosure showed a positive result (violet) for the alkaline phosphatase staining, which is characteristic of embryonic stem cells.

[Example 3] Characterization of Induced Pluripotent Stem Cells (Gene Expression Analysis)

The cultured cells were recovered and total RNA was separated by using the TRIzol reagent (Invitrogen). After synthesizing cDNA through reverse transcription polymerase chain reaction (RT-PCR), PCR was conducted using primers specific for the Nanog and Oct3/4 genes and the GAPDH gene as a control gene. The expression of these genes was analyzed by electrophoresing the PCR product on an agarose gel. The result is shown in FIG. 7.

Figure 7:
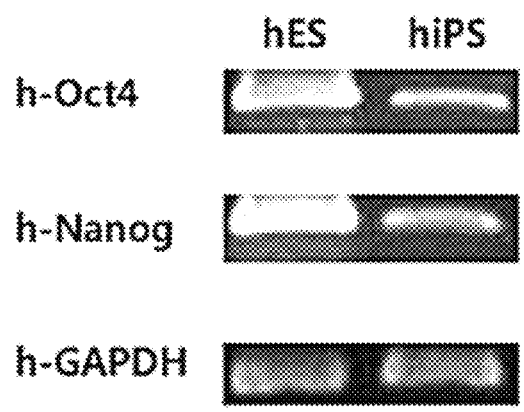
FIG. 7 shows gene expression in pluripotent stem cells induced according to the present disclosure.

As seen from FIG. 7, the pluripotent stem cells (hiPS) induced by the method of the present disclosure showed expression of the Nanog and Oct3/4 genes, which are characteristic of embryonic stem cells (hES).

[Example 4] Preparation of Sequoia (Sequoiadendron giganteum) Callus Extract Containing Shikimic Acid 20 mg of the sequoia callus powder of Example 1 was dissolved in 1 mL of a DMSO solvent. Similarly, 1 g of the sequoia callus powder was dissolved in 10 mL of a mixture solvent of BG and EtOH to prepare a sequoia callus extract containing shikimic acid. The prepared extracts were used as samples in the following test example.

[Test Example 1] Compositional Analysis of Sequoia Callus Extract

Of the sequoia extracts prepared in Example 4, the sequoia callus extract prepared using the mixture solvent of BG and EtOH was subjected to compositional analysis by HPLC.

The compositional analysis of the extract was performed using the Waters 1525μ Binary HPLC pump and the Gemini 5u C18 110 A column (5 μm, 4.6 mm×250 nm, Phenomenex). Solvent A (water, containing 0.1% TFA) and solvent B (acetonitrile, containing 0.1% TFA) were used as mobile phases and a 230-nm UV lamp was used. Measurement was carried out with a flow rate of 1 mL/min, a run time of 46 minutes and an extract injection volume of 20 μL.

Figure 8:
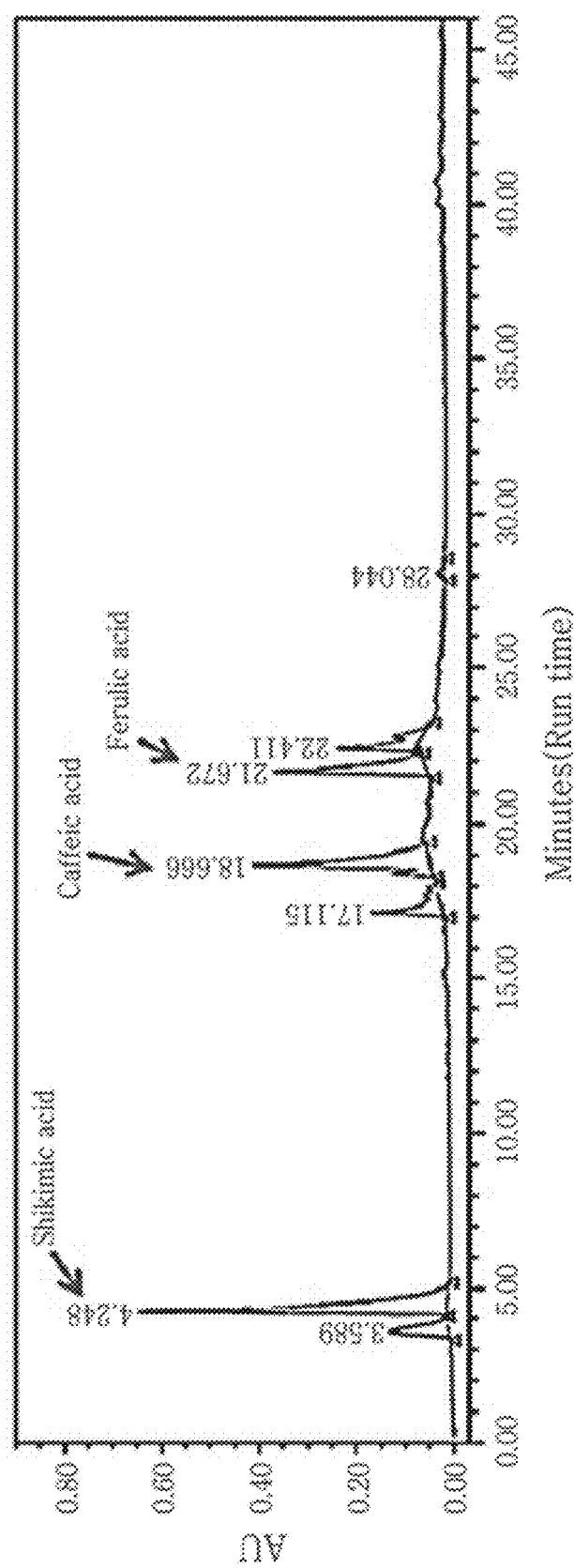
FIG. 8 shows an HPLC result of a *sequoia* callus extract according to the present disclosure. Shikimic acid has a structure of [Chemical Formula 1].
Figure 9:
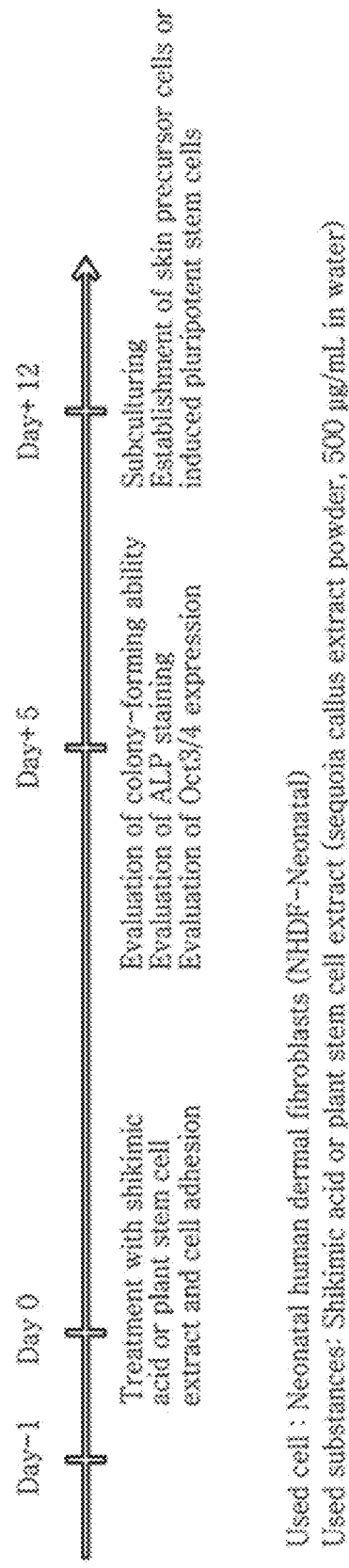
FIG. 9 schematically describes an experimental procedure of inducing pluripotent stem cells using shikimic acid or a plant stem cell extract containing the same according to the present disclosure.

The LC spectrum of the sequoia extract is shown in FIG. 8 and the analysis result is given in Table 1. In Table 1, % Area denotes the percentage (%, w/v) of the substance contained the sequoia extract. It can be seen that the sequoia callus extract contains shikimic acid in a larger amount than any other substance. It can be also seen that the sequoia callus extract contains, in addition to the shikimic acid, caffeic acid and ferulic acid.

TABLE 1

|   | RT | Area | % Area | Height |
| --- | --- | --- | --- | --- |
| 1 | 3.589 | 2413779 | 7.91 | 122548 |
| 2 (shikimic acid) | 4.248 | 9990137 | 32.75 | 633894 |
| 3 | 17.115 | 2660895 | 8.72 | 146243 |
| 4 (caffeic acid) | 18.666 | 7252283 | 23.78 | 363051 |
| 5 (ferulic acid) | 21.672 | 5225473 | 17.13 | 320196 |
| 6 | 22.411 | 2775302 | 9.10 | 159198 |
| 7 | 28.044 | 183049 | 0.60 | 15075 |

Figure 10:
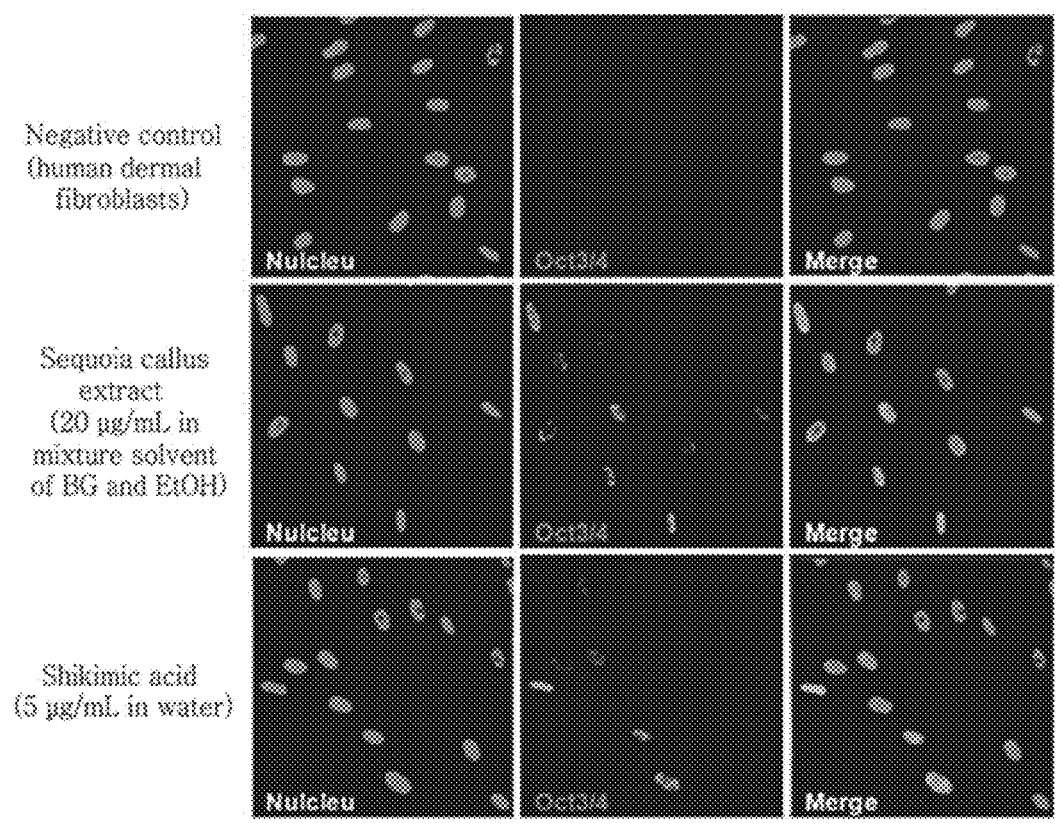
FIG. 10 shows expression of the Oct3/4 gene in HDF after treatment with shikimic acid or a *sequoia* callus extract.

[Test Example 2-1] Increase of Oct 3/4 Expression $5 \times 10^5$ neonatal human dermal fibroblasts (NHDF-Neonatal) (CC-2509, Lonza, USA) were treated with a permeabilization buffer and 10 μg/mL digitonin and then with the 20 μg/mL sequoia callus extract (mixture solvent of BG and EtOH) of Example 4 or 5 μg/mL shikimic acid, respectively. Untreated NHDF-Neonatal were used as a negative control group. On day 3 after the treatment, the cells (5,000 cells) were attached on a 4-chamber slide. Next day, i.e., on day 4, the cells were fixed with 3.8% formaldehyde in PBS (diluted from 38% paraformaldehyde) and kept at room temperature for 10 minutes. Then, 400× images were obtained using the Carl Zeiss Confocal microscope LSM510 by immunocytochemistry using Oct3/4 antibody (Genetex, GTX100622, ×200) and Alexa Fluor® 488 goat anti-rabbit IgG. The obtained images are shown in FIG. 10. The ratio of Oct3/4-positive cells was determined by analyzing the Carl Zeiss Confocal microscopic images obtained from the Oct3/4 ICC experiment, for 4 or more images per sample, 5 on average. The result is shown in Table 2.

TABLE 2

| Treated compound | Number of Oct3/4-positive cells (per image) | | | | | Number of total cells (per image) | | | | | Ratio of Oct3/4-positive cells | | | | | Ratio of Oct3/4-positive cells (%) | |
|---|---|---|---|---|---|---|---|---|---|---|---|---|---|---|---|---|---|
| | #1 | #2 | #3 | #4 | #5 | #1 | #2 | #3 | #4 | #5 | #1 | #2 | #3 | #4 | #5 | Mean | SD |
| Negative control | 0 | 0 | 0 | 0 | 0 | 11 | 6 | 17 | 20 | 13 | 0.0 | 0.0 | 0.0 | 0.0 | 0.0 | 0% | 0% |
| 20 μg/mL sequoia callus extract (BG + EtOH) | 0 | 3 | 4 | 6 | 3 | 6 | 6 | 10 | 13 | 11 | 0.0 | 0.5 | 0.4 | 0.5 | 0.3 | 33% | 5% |
| 5 μg/mL shikimic acid (water) | 2 | 4 | 1 | 5 | | 12 | 14 | 7 | 9 | | 0.2 | 0.3 | 0.1 | 0.6 | | 29% | 5% |

As can be seen from FIG. 10, the HDF treated with the *sequoia* callus extract of Example 4 showed increased expression of the Oct3/4 gene as compared to the normal HDF (negative control), which was higher than those treated with shikimic acid.

Also, as can be seen from Table 2, the percentage of the cells positive for the Oct3/4 gene was the highest as 33% for the *sequoia* callus extract extracted with a mixture solvent of BG (butylene glycol) and EtOH, which was higher than that for shikimic acid.

Figure 11:
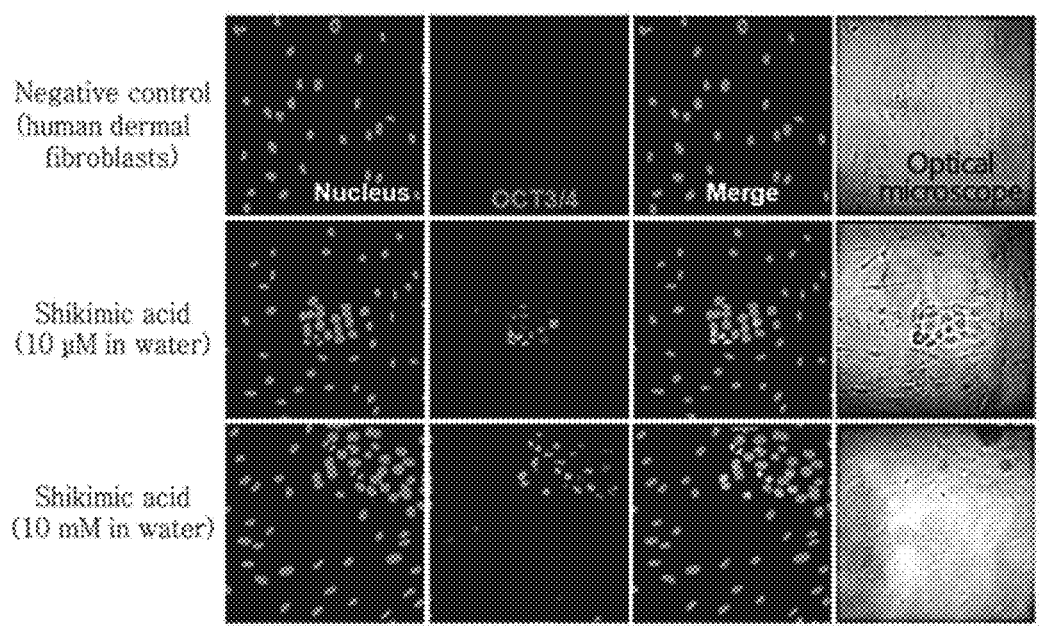
FIG. 11 shows expression of the Oct3/4 gene in HDF after treatment with shikimic acid at different concentrations.

[Test Example 2-2] Increase of Oct 3/4 Expression $1 \times 10^6$ neonatal human dermal fibroblasts (NHDF-Neonatal) (CC-2509, Lonza, USA) were treated with 10 μM or 10 mM shikimic acid, respectively. Untreated NHDF-Neonatal were used as a negative control group. On day 5 after the treatment, the cells (5,000 cells) were attached on a 4-chamber slide. 3 days later, i.e., on day 8, the cells were fixed with 3.8% formaldehyde in PBS (diluted from 38% paraformaldehyde) and kept at room temperature for 10 minutes. Then, 400× images were obtained using the Carl Zeiss Confocal microscope LSM510 by immunocytochemistry using Oct3/4 antibody (Genetex, GTX100622, ×200) and Alexa Fluor® 488 goat anti-rabbit IgG. The obtained images are shown in FIG. 11. The ratio of Oct3/4-positive cells was determined by analyzing the Carl Zeiss Confocal microscopic images obtained from the Oct3/4 ICC experiment, for 4 or more images per sample, 5 on average. The result is shown in Table 3.

when treated with the shikimic acid in water. The value was significantly higher as compared to the untreated group.

From the above results, it was confirmed that the shikimic acid which is the main ingredient of the *sequoia* callus extract is effective in increasing the expression of the Oct3/4 gene which plays a critical role in inducing induced pluripotent stem cells. Accordingly, by injecting the shikimic acid or the extract containing the same according to the present disclosure into somatic cells, the induction of induced pluripotent stem cells can be induced through expression of the Oct3/4 gene.

[Test Example 3-1] Increase of Expression of Stem Cell Marker Alkaline Phosphatase (ALP)

Figure 12:
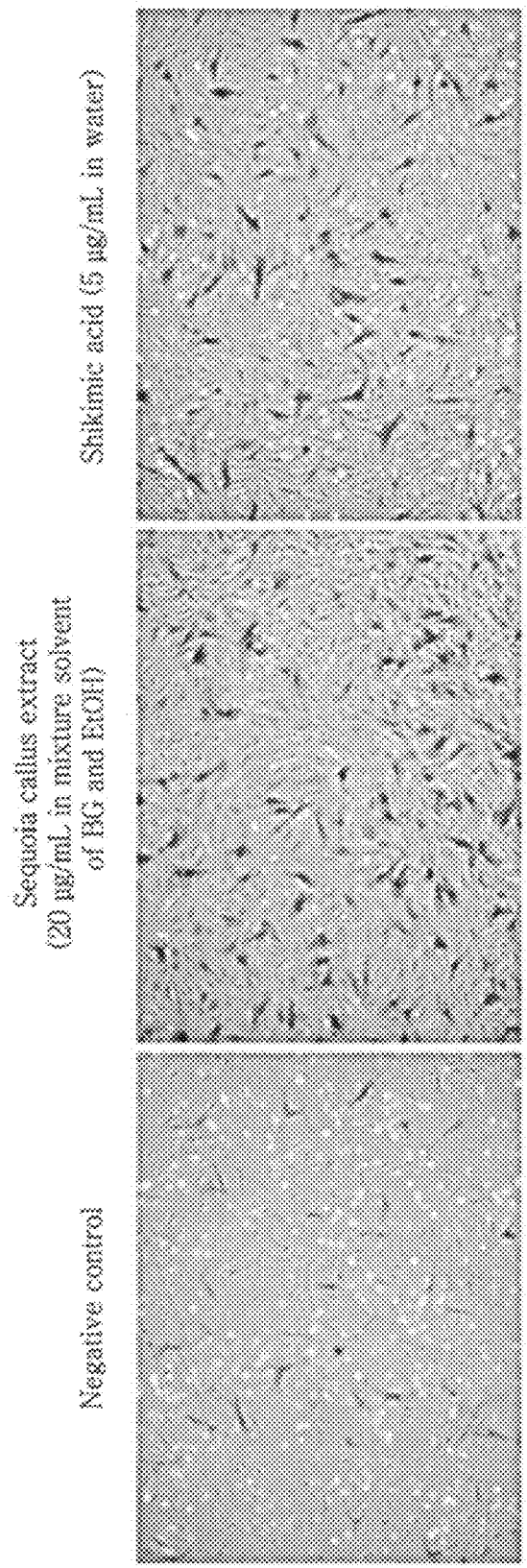
FIG. 12 shows increased expression of ALP after treatment with shikimic acid or a *sequoia* callus extract.

$5 \times 10^5$ NHDF-Neonatal (CC-2509, Lonza, USA) were treated with a permeabilization buffer and 10 μg/mL digitonin and then with the 20 μg/mL *sequoia* callus extract (mixture solvent of BG and EtOH) of Example 4 or 5 μg/mL shikimic acid, respectively. Untreated NHDF-Neonatal were used as a negative control group. On day 6 after the treatment, the cells (5,000 cells) were attached on a 12-well plate. 5 days later, i.e., on day 11, the cells were fixed with 3.8% formaldehyde in PBS and kept at room temperature for 15 minutes. Then, the cells were treated with 200 μL of the NBT/BCIP® ALP substrate solution diluted in 10 mL of ALP buffer, with 0.5 mL each time. 20 hours later, the cells were observed under the Olympus CKX41 optical microscope at 40× magnification. The result is shown in FIG. 12.

TABLE 3

| | | Number of Oct3/4-positive cells (per image) | | | | | Number of total cells (per image) | | | | | Ratio of Oct3/4-positive cells | | | | | Ratio of Oct3/4-positive cells (%) | |
|---|---|---|---|---|---|---|---|---|---|---|---|---|---|---|---|---|---|---|
| | | #1 | #2 | #3 | #4 | #5 | #1 | #2 | #3 | #4 | #5 | #1 | #2 | #3 | #4 | #5 | Mean | SD |
| Negative control | | 0 | 0 | 0 | 0 | 0 | 11 | 6 | 17 | 20 | 13 | 0.0 | 0.0 | 0.0 | 0.0 | 0.0 | 0% | 0% |
| Shikimic acid (water) | 10 μM | 18 | 4 | 10 | 14 | 24 | 54 | 27 | 33 | 53 | 60 | 0.33 | 0.15 | 0.30 | 0.26 | 0.40 | 29% | 2% |
| | 10 mM | 11 | 11 | 12 | 0 | 18 | 33 | 32 | 59 | 36 | 39 | 0.33 | 0.34 | 0.20 | 0.00 | 0.46 | 27% | 4% |

As can be seen from FIG. 11, the HDF treated with shikimic acid showed increased expression of the Oct3/4 gene as compared to the untreated normal HDF. The Oct3/4 gene expression increased with the concentration of shikimic acid.

Also, as can be seen from Table 3, the percentage of the cells positive for the Oct3/4 gene was 27-29% on average As can be seen from FIG. 12, the HDF treated with the *sequoia* callus extract showed a larger stained area than the normal HDF, suggesting that the expression of ALP was increased remarkably. Also, it can be seen that the cells treated with the *sequoia* callus extract showed higher ALP expression than those treated with the shikimic acid.

During the process in which fibroblasts are converted to induced pluripotent stem cells, ALP is begin to be expressed 3 day after the genes such as Oct4 are expressed in the cells. It is a marker known to play an important role in the early stage of formation of dedifferentiated stem cells. Therefore, when the *sequoia* callus extract according to the present disclosure is injected into somatic cells, the expression of ALP increases remarkably and the Oct4 gene is expressed. Accordingly, induced pluripotent stem cells can be induced.

From this experimental result, it was confirmed that the *sequoia* callus extract according to the present disclosure exhibits a remarkable effect of activating stem cells by promoting the expression of the stem cell marker ALP.

[Test Example 3-2] Increase of Expression of Stem Cell Marker Alkaline Phosphatase (ALP)

$1 \times 10^6$ NHDF-Neonatal (CC-2509, Lonza, USA) were treated with 10 μM or 10 mM shikimic acid, respectively. Untreated NHDF-Neonatal were used as a negative control group. On day 5 after the treatment, the cells (100,000 cells) were attached on a 6-well plate. 7 days later, i.e., on day 12, the cells were fixed with 3.8% formaldehyde in PBS and kept at room temperature for 15 minutes. Then, the cells were treated with 200 μL of the NBT/BCIP® ALP substrate solution diluted in 10 mL of ALP buffer, with 0.5 mL each time. 20 hours later, the cells were observed under the Olympus CKX41 optical microscope at 40× magnification. The result is shown in FIG. 13.

Figure 13:
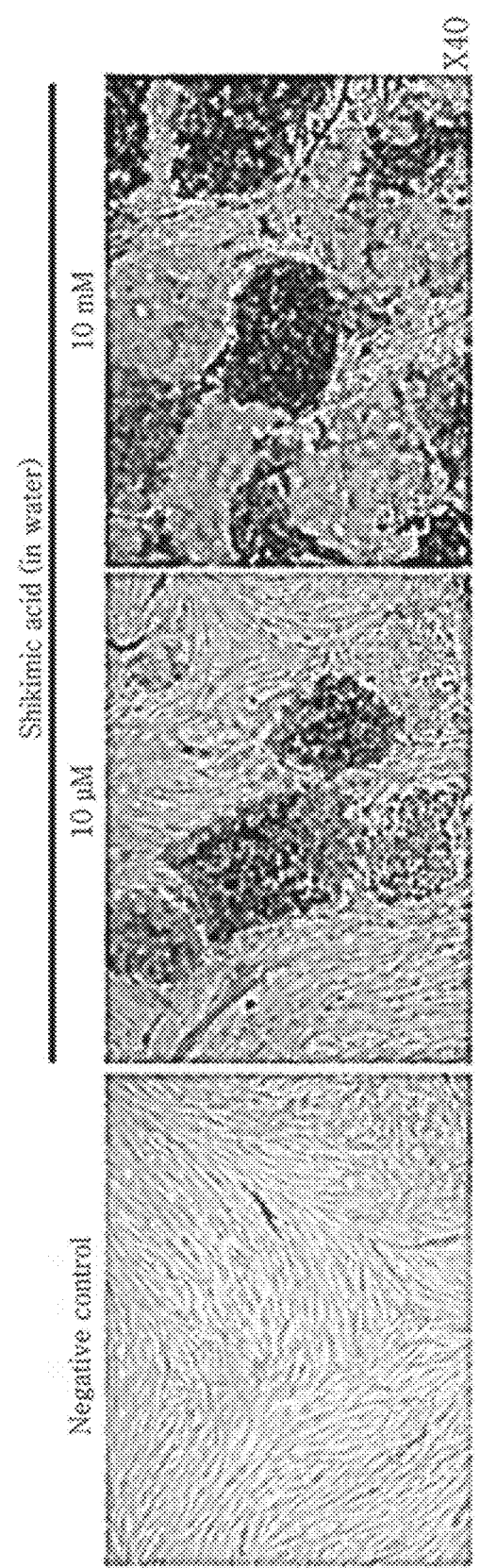
FIG. 13 shows increased expression of ALP after treatment with shikimic acid at different concentrations.

As can be seen from FIG. 13, the HDF treated with the shikimic acid showed a larger area stained deep blue than the normal HDF, suggesting that the expression of ALP was increased remarkably. Also, it can be seen that the cells treated with the shikimic acid showed higher ALP expression than those treated with the shikimic acid.

During the process in which fibroblasts are converted to induced pluripotent stem cells, ALP is begin to be expressed 3 day after the genes such as Oct4 are expressed in the cells. It is a marker known to play an important role in the early stage of formation of dedifferentiated stem cells. Therefore, when the shikimic acid and a plant extract containing the same according to the present disclosure is injected into somatic cells, the expression of ALP increases remarkably and the Oct4 gene is expressed. Accordingly, induced pluripotent stem cells can be induced.

From this experimental result, it was confirmed that the shikimic acid and a plant extract containing the same according to the present disclosure exhibits a remarkable effect of activating stem cells by promoting the expression of the stem cell marker ALP.

Figure 14:
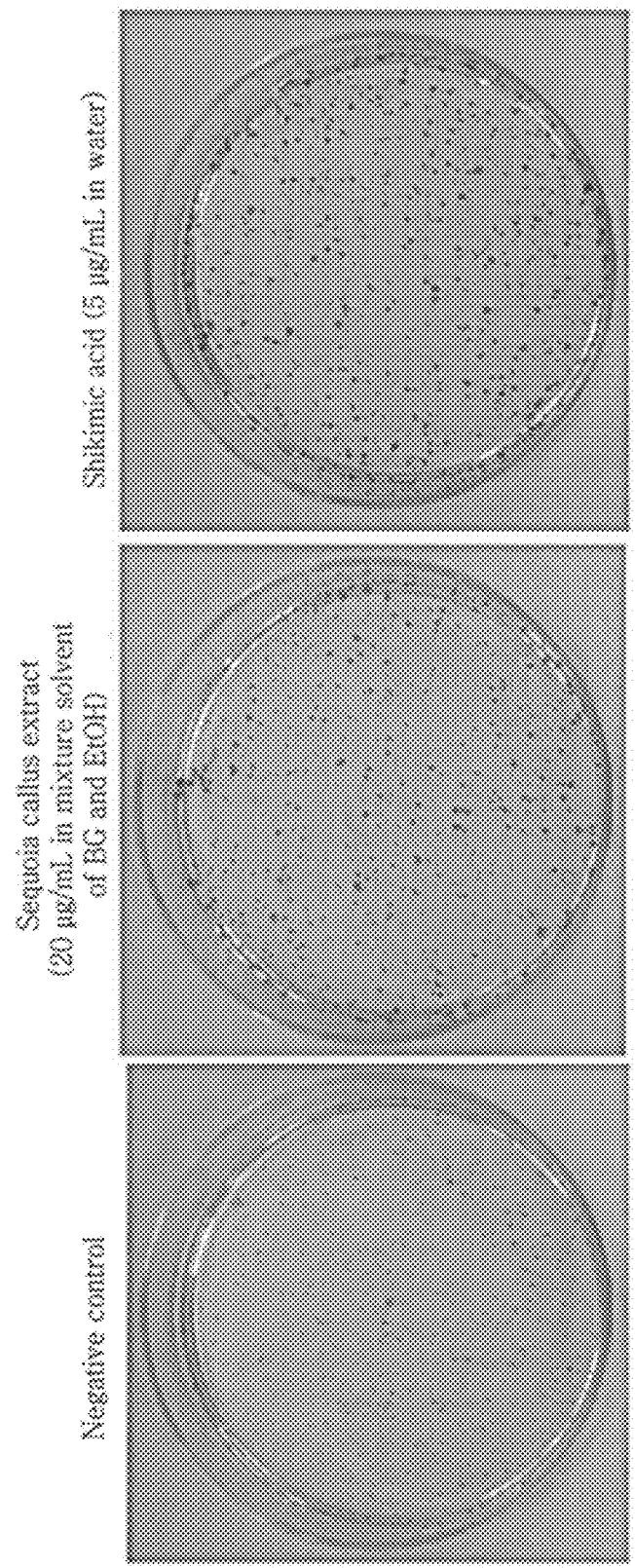
FIG. 14 shows the colony-forming ability of dermal cells after treatment with shikimic acid or a *sequoia* callus extract.

[Test Example 4-1] Increase of Colony-Forming Ability of Dermal Cells $5 \times 10^5$ NHDF-Neonatal (CC-2509, Lonza, USA) were treated with a permeabilization buffer and 10 μg/mL digitonin and then with the 100 ppm or 200 ppm *sequoia* callus extract (mixture solvent of BG and EtOH) of Example 4, which had been filtered through a 0.4-μm filter, and a 20 ppm DMSO solution. Untreated NHDF-Neonatal were used as a negative control group. On day 10 after subculturing, the cells (200 cells) were attached on a 60-mm plate. On day 23, the cells were washed with ice-cold PBS and then fixed with ice-cold methanol kept at −20° C. for 10 minutes. The cells were stained by treating for 5-10 minutes with a working solution, which had been prepared by diluting 1% crystal violet in an ethanol stock solution 1/10 with PBS, washed 4 times with PBS and then imaged. For quantitative analysis, the cells were eluted by treating with an elution buffer consisting of 50% ethanol, 40% DW, and 10% acetic acid for 5 minutes. Then, absorbance was measured at 580 nm after transferring 200 μL of the cells to a 96-well plate. The obtained images are shown in FIG. 14. And, the result of absorbance measurement relative to the negative control group is shown in FIG. 16.

As can be seen from FIG. 14, the cells treated with the *sequoia* callus extract showed a larger stained area than the negative control group NHDF-Neonatal, suggesting that the dermal cells differentiated actively and formed a large colony.

Figure 16:
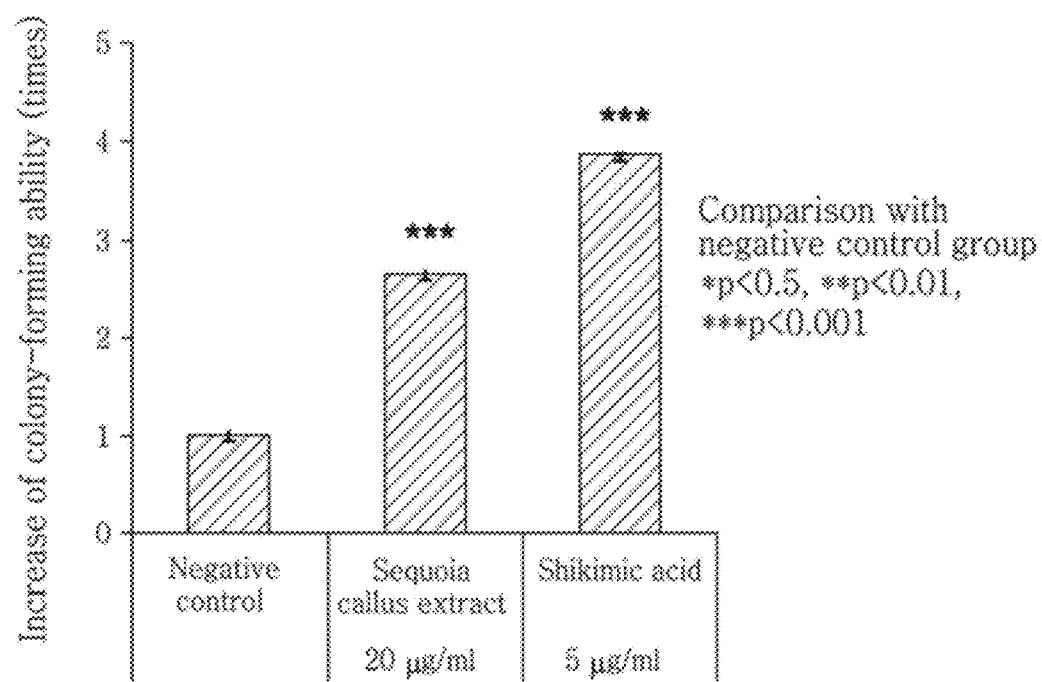
FIG. 16 shows the colony-forming ability of dermal cells after treatment with shikimic acid or a *sequoia* callus extract.

Also, as can be seen from FIG. 16, the cells treated with the *sequoia* callus extract showed about 2.6 times increased colony-forming ability as compared to the negative control group, which is statistically significant. The cells treated with the shikimic acid showed increase of about 3.8 times as compared to the negative control group.

Accordingly, it was confirmed that the *sequoia* callus extract according to the present disclosure remarkably promotes the proliferation of fibroblasts.

Also, it was confirmed that the *sequoia* extract according to the present disclosure promotes skin regeneration by remarkably promoting the proliferation of fibroblasts.

Figure 15:
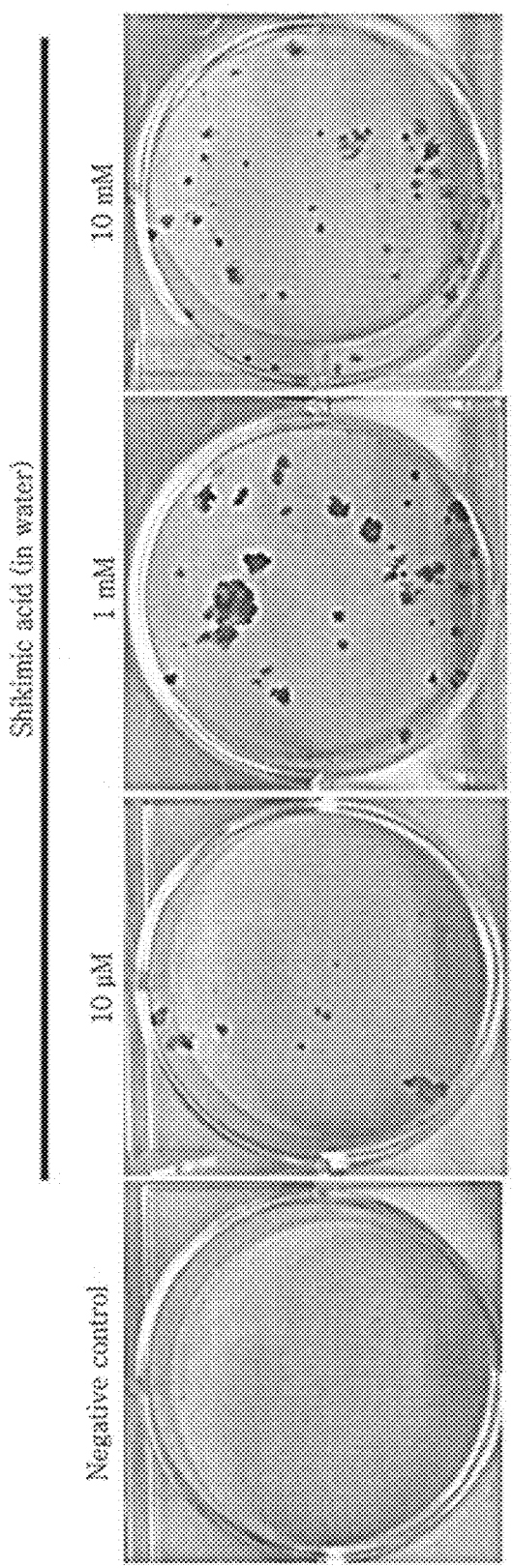
FIG. 15 shows the colony-forming ability of dermal cells after treatment with shikimic acid different concentrations.

[Test Example 4-2] Increase of Colony-Forming Ability of Dermal Cells $1 \times 10^6$ NHDF-Neonatal (CC-2509, Lonza, USA) were treated with 10 μM, 50 μM, 100 μM, 1 mM or 10 mM shikimic acid, respectively. Untreated NHDF-Neonatal were used as a negative control group. On day 5 after subculturing, the cells (200 cells) were attached on a 60-mm plate. On day 17, the cells were washed with ice-cold PBS and then fixed with ice-cold methanol kept at −20° C. for 10 minutes. The cells were stained by treating for 5-10 minutes with a working solution, which had been prepared by diluting 1% crystal violet in an ethanol stock solution 1/10 with PBS, washed 4 times with PBS and then imaged. For quantitative analysis, the cells were eluted by treating with an elution buffer consisting of 50% ethanol, 40% DW, and 10% acetic acid for 5 minutes. Then, absorbance was measured at 580 nm after transferring 200 μL of the cells to a 96-well plate. The obtained images are shown in FIG. 15. And, the result of absorbance measurement relative to the negative control group is shown in FIG. 17.

As can be seen from FIG. 15, the cells treated with the shikimic acid showed a larger stained area than the negative control group NHDF-Neonatal, suggesting that the dermal cells differentiated actively and formed a large colony.

Figure 17:
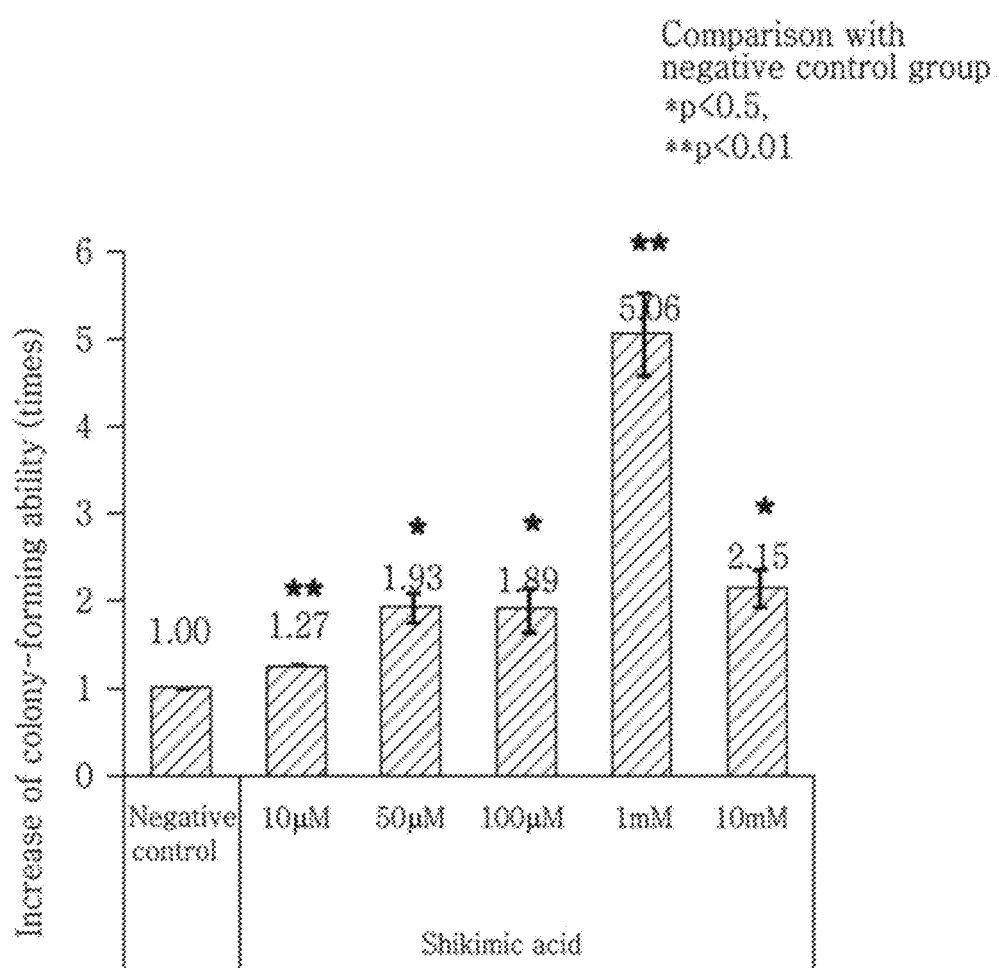
FIG. 17 shows the colony-forming ability of dermal cells after treatment with shikimic acid different concentrations.

Also, as can be seen from FIG. 17, the cells treated with the shikimic acid showed about 1.27-5.06 times increased colony-forming ability as compared to the negative control group, which is statistically significant. In particular, the cells treated with 1 mM shikimic acid showed the most increase in colony-forming ability. Therefore, it can be seen that treatment with 1 mM shikimic acid leads to the most promotion of cellular proliferation.

Accordingly, it was confirmed that the shikimic acid according to the present disclosure remarkably promotes the proliferation of fibroblasts.

Also, it was confirmed that the shikimic acid according to the present disclosure promotes skin regeneration by remarkably promoting the proliferation of fibroblasts.

[Test Example 5] Increase of Proliferating Ability of Dermal Cells 2,000 NHDF-Neonatal (CC-2509, Lonza, USA) were attached on a 96-well plate. The next day, the cells were treated with the 20 μg/mL *sequoia* callus extract (mixture solvent of BG and EtOH) of Example 4 and 5 μg/mL shikimic acid. Untreated NHDF-Neonatal were used as a negative control group. Then, we were subculturing it for 7 days (as confluency becomes to 90% or below on $7^{th}$ day). After 6 days later, 10 μL of WST-1 was treated and absorbance was measured at 450 nm. The result relative to the negative control group is shown in FIG. 18.

Figure 18:
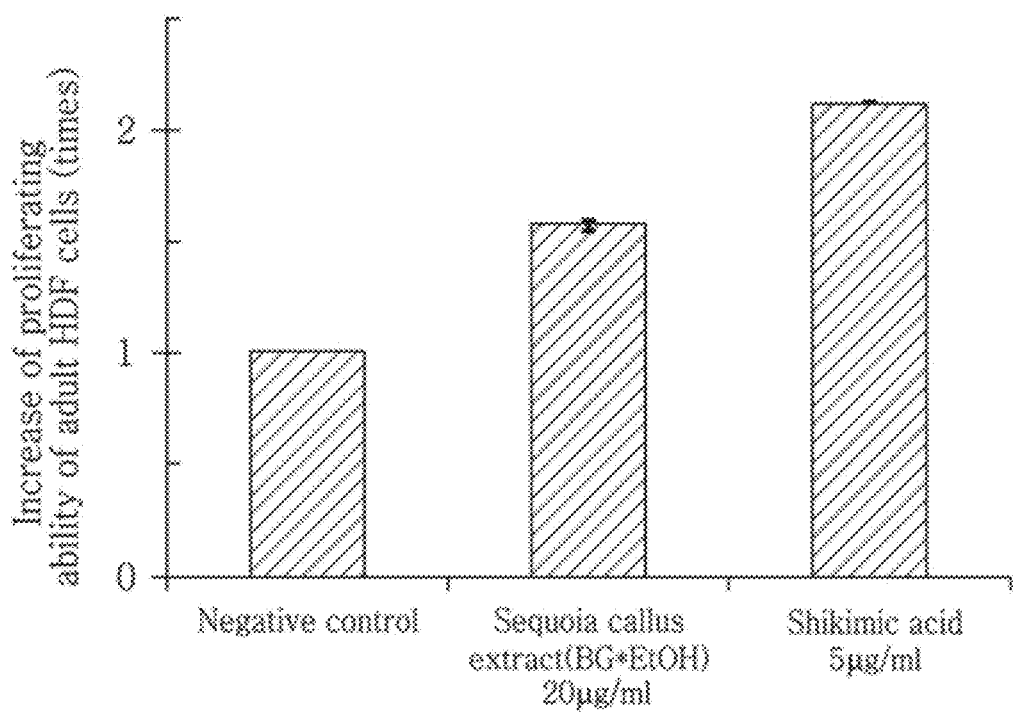
FIG. 18 shows increased proliferating ability of dermal cells after treatment with shikimic acid or a *sequoia* callus extract.

As can be seen from FIG. 18, treatment with the *sequoia* callus extract according to the present disclosure resulted in about 1.5 times or more increased cell division as compared to the negative control group, which is statistically significant. And, the shikimic acid resulted in 2 times increased cell division as compared to the normal control group.

Accordingly, it was confirmed that the *sequoia* callus extract according to the present disclosure promotes the cell division of fibroblasts remarkably.

Also, it was confirmed that the *sequoia* extract according to the present disclosure promotes skin regeneration by remarkably promoting the cell division of fibroblasts.

The foregoing description of the present disclosure is for the purpose of illustration only and those of ordinary skill in the art to which the present disclosure belongs will understand that the changes can be easily made thereto without departing from the technical spirit and scope of this disclosure. Therefore, the above-described examples should be interpreted as being exemplary.

Hereinafter, the formulation examples of the composition will be described. However, the following formulation examples are for illustrative purposes only.

[Formulation Example 1] Soft Capsule

40 μg of shikimic acid or the *sequoia* callus extract of Example 4, 9 mg of vitamin E, 9 mg of vitamin C, 2 mg of palm oil, 8 mg of hydrogenated vegetable oil, 4 mg of yellow beeswax and 9 mg of lecithin were mixed according to a commonly employed method, and 400 mg of the mixture was filled per capsule. Separately from this, a soft capsule sheet was prepared from 66 parts by weight of gelatin, 24 parts by weight of glycerin and 10 parts by weight of a sorbitol solution and the mixture was filled therein to prepare a soft capsule in which 400 mg of the composition according to the present disclosure is contained.

[Formulation Example 2] Tablet

40 μg of shikimic acid or the *sequoia* callus extract of Example 4, 9 mg of vitamin E, 9 mg of vitamin C, 200 mg of galactooligosaccharide, 60 mg of lactose and 140 mg of maltose were mixed and granulated using a fluidized-bed dryer. After adding 6 mg of sugar ester, 500 mg of the resulting composition was prepared into a tablet according to a commonly employed method.

[Formulation Example 3] Drink

40 μg of shikimic acid or the *sequoia* callus extract of Example 4, 9 mg of vitamin E, 9 mg of vitamin C, 10 g of glucose, 0.6 g of citric acid and 25 g of oligosaccharide syrup were mixed. After adding 300 mL of purified water, 200 mL of the mixture was filled per bottle and sterilized at 130° C. for 4-5 seconds.

[Formulation Example 4] Granule

40 μg of shikimic acid or the *sequoia* callus extract of Example 4, 9 mg of vitamin E, 9 mg of vitamin C, 250 mg of anhydrous crystalline glucose and 550 mg of starch were mixed, granulated using a fluidized-bed granulator and then filled in a pouch.

[Formulation Example 5] Injection

An injection (for 2-mL ampoule) was prepared according to a commonly employed method as described in Table 4.

TABLE 4

| Ingredients | Contents |
| --- | --- |
| Shikimic acid or sequoia callus extract of Example 4 | 40 μg |
| Sterile distilled water for injection | adequate |
| pH control agent | adequate |

[Formulation Example 6] Softening Lotion (Skin Lotion)

A softening lotion was prepared according to a commonly employed method as described in Table 5.

TABLE 5

| Ingredients | Contents (wt %) |
| --- | --- |
| Shikimic acid or sequoia callus extract of Example 4 | 0.2 |
| Glycerin | 3.0 |
| Butylene glycol | 2.0 |
| Propylene glycol | 2.0 |
| Carboxyvinyl polymer | 0.1 |
| PEG-12 nonyl phenyl ether | 0.2 |
| Polysorbate 80 | 0.4 |
| Ethanol | 10.0 |
| Triethanolamine | 0.1 |
| Preservative, pigment and fragrance | adequate |
| Purified water | balance |

[Formulation Example 7] Nourishing Lotion (Milk Lotion)

A nourishing lotion was prepared according to a commonly employed method as described in Table 6.

TABLE 6

| Ingredients | Contents (wt %) |
| --- | --- |
| Shikimic acid or sequoia callus extract of Example 4 | 1.0 |
| Glycerin | 3.0 |
| Butylene glycol | 3.0 |
| Propylene glycol | 3.0 |
| Carboxyvinyl polymer | 0.1 |
| Beeswax | 4.0 |
| Polysorbate 60 | 1.5 |
| Caprylic/capric triglyceride | 5.0 |
| Squalane | 5.0 |
| Sorbitan sesquioleate | 1.5 |
| Liquid paraffin | 0.5 |
| Cetearyl alcohol | 1.0 |
| Triethanolamine | 0.2 |

TABLE 6-continued

| Ingredients | Contents (wt %) |
|---|---|
| Preservative, pigment and fragrance | adequate |
| Purified water | balance |

[Formulation Example 8] Nourishing Cream

A nourishing cream was prepared according to a commonly employed method as described in Table 7.

TABLE 7

| Ingredients | Contents (wt %) |
|---|---|
| Shikimic acid or sequoia callus extract of Example 4 | 2.0 |
| Glycerin | 3.0 |
| Butylene glycol | 3.0 |
| Liquid paraffin | 7.0 |
| Beta-glucan | 7.0 |
| Carbomer | 0.1 |
| Caprylic/capric triglyceride | 3.0 |
| Squalane | 5.0 |
| Cetearyl glucoside | 1.5 |
| Sorbitan stearate | 0.4 |
| Polysorbate 60 | 1.2 |
| Triethanolamine | 0.1 |
| Preservative, pigment and fragrance | adequate |
| Purified water | balance |

[Formulation Example 9] Massage Cream

A massage cream was prepared according to a commonly employed method as described in Table 8.

TABLE 8

| Ingredients | Contents (wt %) |
|---|---|
| Shikimic acid or sequoia callus extract of Example 4 | 2.0 |
| Glycerin | 8.0 |
| Butylene glycol | 4.0 |
| Liquid paraffin | 45.0 |
| Beta-glucan | 7.0 |
| Carbomer | 0.1 |
| Caprylic/capric triglyceride | 3.0 |
| Beeswax | 4.0 |
| Cetearyl glucoside | 1.5 |
| Sorbitan sesquioleate | 0.9 |
| Vaseline | 3.0 |
| Paraffin | 1.5 |
| Preservative, pigment and fragrance | adequate |
| Purified water | balance |

[Formulation Example 10] Pack

A pack was prepared according to a commonly employed method as described in Table 9.

TABLE 9

| Ingredients | Contents (wt %) |
|---|---|
| Shikimic acid or sequoia callus extract of Example 4 | 0.2 |
| Glycerin | 4.0 |
| Polyvinyl alcohol | 15.0 |
| Hyaluronic acid extract | 5.0 |
| Beta-glucan | 7.0 |
| Allantoin | 0.1 |
| Nonyl phenyl ether | 0.4 |
| Polysorbate 60 | 1.2 |

TABLE 9-continued

| Ingredients | Contents (wt %) |
|---|---|
| Ethanol | 6.0 |
| Preservative, pigment and fragrance | adequate |
| Purified water | balance |

[Formulation Example 11] Health Food

A health food was prepared according to a commonly employed method as described in Table 10.

TABLE 10

| Ingredients | Contents |
|---|---|
| Shikimic acid or sequoia callus extract of Example 4 | 20 μg |
| Vitamin A acetate | 70 μg |
| Vitamin E | 1.0 mg |
| Vitamin $B_1$ | 0.13 mg |
| Vitamin $B_2$ | 0.15 mg |
| Vitamin $B_6$ | 0.5 mg |
| Vitamin $B_{12}$ | 0.2 μg |
| Vitamin C | 10 mg |
| Biotin | 10 μg |
| Nicotinamide | 1.7 mg |
| Folic acid | 50 μg |
| Calcium pantothenate | 0.5 mg |
| Ferrous sulfate | 1.75 mg |
| Zinc oxide | 0.82 mg |
| Magnesium carbonate | 25.3 mg |
| Monobasic potassium phosphate | 15 mg |
| Dibasic calcium phosphate | 55 mg |
| Potassium citrate | 90 mg |
| Calcium carbonate | 100 mg |
| Magnesium chloride | 24.8 mg |

The above-described composition of the mixture of vitamins and minerals is only exemplary and may be changed as desired.

[Formulation Example 12] Health Drink

A health drink was prepared according to a commonly employed method as described in Table 11.

TABLE 11

| Ingredients | Contents |
|---|---|
| Shikimic acid or sequoia callus extract of Example 4 | 20 μg |
| Citric acid | 1000 mg |
| Oligosaccharide | 100 g |
| Taurine | 1 g |
| Purified water | balance |

According to a commonly employed health drink preparation method, the above ingredients were mixed and heated at 85° C. for about 1 hour under stirring. The resulting solution was filtered and sterilized.

[Formulation Example 13] Injection Containing Pluripotent Stem Cells

An injection containing pluripotent stem cells was prepared according to a commonly employed method as described in Table 12.

TABLE 12

| Ingredients | Contents |
|---|---|
| Pluripotent stem cells of Example 2 | 40 μg |
| Sterile distilled water for injection | adequate |
| pH control agent | adequate |

While the exemplary embodiments have been shown and described, it will be understood by those skilled in the art that various changes in form and details may be made thereto without departing from the spirit and scope of this disclosure as defined by the appended claims.

The invention claimed is:

1. A method for activating stem cells, proliferating skin cells, or regenerating skin, comprising a step of
    administering a composition containing at least one selected from the group consisting of shikimic acid, a plant extract comprising shikimic acid, and a plant stem cell extract comprising shikimic acid to an individual in need of activation of stem cells, proliferation of skin cells, or skin regeneration,
    wherein skin regeneration is dermal cell differentiation,
    wherein the composition comprises shikimic acid at a concentration of 0.8 mM to 5 mM based on the total volume of the composition.

2. The method according to claim 1, wherein the composition comprises the plant extract or the plant stem cell extract at a concentration of 0.001 μg/mL to 2 mg/mL, based on the total volume of the composition.

3. The method according to claim 1, wherein the composition is a pharmaceutical composition or a cosmetic composition.

* * * * *